United States Patent [19]

Scheunemann et al.

[11] Patent Number: 4,762,848

[45] Date of Patent: Aug. 9, 1988

[54] 1,3-THIAZOLES AND THEIR USE AS IMMUNOMODULATORS

[75] Inventors: Karl-Heinz Scheunemann, Frankfurt am Main; Walter Dürckheimer, Hattersheim am Main; Jürgen Blumbach, Frankfurt am Main; Michael Limbert, Hofheim am Taunus; Hans-Ulrich Schorlemmer, Marburg; Gerhard Dickneite, Marburg; Hans-Harald Sedlacek, Marburg, all of Fed. Rep. of Germany

[73] Assignee: Hoechst Aktiengesellschaft, Frankfurt, Fed. Rep. of Germany

[21] Appl. No.: 837,700

[22] Filed: Mar. 10, 1986

[30] Foreign Application Priority Data

Mar. 12, 1985 [DE] Fed. Rep. of Germany ....... 3508665

[51] Int. Cl.$^4$ .................... A61K 31/38; C07D 277/34; C07D 277/36; C07D 213/62

[52] U.S. Cl. .................................. 514/369; 548/182; 548/183; 548/184; 548/185; 548/186; 548/187; 548/188; 548/189; 548/127; 548/128; 548/129; 548/130; 548/132; 548/135; 548/136; 548/138; 548/144; 548/161; 548/165; 548/169; 548/170; 548/171; 548/213; 548/217; 548/221; 548/222; 548/225; 548/226; 548/228; 548/229; 548/230; 548/231; 548/232; 548/243; 548/244; 548/255; 548/263; 548/264; 548/265; 548/251; 548/301; 548/305; 548/329; 548/337; 548/358; 548/363; 548/365; 548/367; 548/375; 548/376; 549/62; 549/63; 549/64; 549/65; 549/66; 549/475; 549/476; 549/477; 549/478; 549/479; 544/315; 544/316; 544/317; 544/318; 544/319; 544/320; 544/406; 544/408; 544/182; 544/213; 544/215; 544/216; 544/219; 544/220; 544/239; 544/240; 544/298; 544/309; 544/311; 544/312; 546/290; 546/291; 546/292; 546/296; 546/297; 546/298; 546/300; 546/301

[58] Field of Search ............... 548/182, 186, 183, 184, 548/185, 187, 188, 189; 514/369

[56] References Cited

U.S. PATENT DOCUMENTS

| | | | |
|---|---|---|---|
| 2,776,976 | 1/1957 | D'Amico | 548/182 |
| 2,886,487 | 5/1959 | Kupferberg et al. | 548/183 |
| 3,558,775 | 1/1971 | Fournier | 548/182 |
| 3,629,473 | 12/1971 | Doebel et al. | 548/182 |
| 3,671,643 | 6/1972 | Kalopissis | 548/182 |
| 3,907,822 | 9/1975 | Narayanan et al. | 548/183 |
| 3,950,542 | 4/1976 | Kalopissis et al. | 548/183 |
| 3,962,237 | 2/1976 | Boyle et al. | 260/247.1 M |
| 3,984,426 | 10/1976 | Winkelmann et al. | 548/182 |
| 4,002,624 | 1/1977 | Trepanier | 260/248 AS |
| 4,018,923 | 4/1977 | Lacefield et al. | 548/182 |
| 4,022,607 | 5/1977 | Jackson | 548/182 |
| 4,035,492 | 7/1977 | Kalopissis et al. | 548/182 |
| 4,065,584 | 12/1977 | Lafon | 548/182 |
| 4,097,669 | 6/1978 | Reisdorff et al. | 548/182 |
| 4,107,438 | 8/1978 | Lafor | 548/182 |
| 4,139,635 | 2/1979 | Kalopissis | 548/182 |
| 4,157,392 | 6/1979 | Gullo et al. | 548/182 |
| 4,197,307 | 4/1980 | Gallay et al. | 548/182 |
| 4,202,901 | 5/1980 | Finch et al. | 424/263 |
| 4,251,527 | 2/1981 | Gullo et al. | 548/183 |
| 4,379,159 | 4/1983 | Cherkofsky | 548/182 |
| 4,396,625 | 8/1983 | Yamanori et al. | 548/182 |
| 4,447,440 | 5/1984 | Busse et al. | 548/182 |

FOREIGN PATENT DOCUMENTS

| | | | |
|---|---|---|---|
| 238200 | 3/1963 | Austria | 548/182 |
| 363076 | 12/1980 | Austria | 548/182 |
| 367296 | 5/1981 | Austria | 548/183 |
| 0093908 | 11/1983 | European Pat. Off. | 548/182 |
| 0137426 | 4/1985 | European Pat. Off. | 548/182 |
| 1667902 | 2/1967 | Fed. Rep. of Germany | 548/183 |
| 2129012 | 6/1971 | Fed. Rep. of Germany | 548/183 |
| 2165554 | 7/1973 | Fed. Rep. of Germany | 548/182 |
| 2533605 | 2/1977 | Fed. Rep. of Germany | 548/182 |
| 2634409 | 2/1977 | Fed. Rep. of Germany | 548/182 |
| 601M | 6/1961 | France | 548/188 |
| 0837278 | 11/1962 | France | 548/183 |
| 2368278 | 10/1976 | France | 548/183 |
| 645806 | 10/1984 | Switzerland | 548/183 |
| 1152814 | 3/1967 | United Kingdom | 548/182 |
| 1604084 | 5/1977 | United Kingdom | 548/183 |
| 2098203 | 11/1982 | United Kingdom | 548/182 |

OTHER PUBLICATIONS

Chem. Abstracts, vol. 78; 71986x (1973).
Chem. Abstracts, vol. 97; 182418a (1982).
J. Heterocyclic Chem., vol. 5, pp. 387-391 (1968).
Progress in Drug Research, vol. 16, pp. 93-119 (1972).
Schleupner et al., Infection & Immunity, vol. 21, No. 3 (1978), pp. 886-895.
Johnson et al., Cancer Immunol., Immuno. Ther. 3, 219-227 (1978).
Kino et al., The J. of Antibiotics, Jul. 1985, pp. 936-940.
Foye, W., Principles of Medicinal Chemistry, 2nd Ed (1981), pp. 101, 102, 850, 851.
Mayer et al., Infection, 8 (1980) No. 1, pp. 1'21.
Bicker et al., J. Infectious Diseases, vol. 139, No. 1 (1979).
Watanabe et al., J. of Antibiotics, vol. 38, No. 2, pp. 1781-1787.
Goodman et al., The Pharmacological Basis of Therapeutics, 6 ed. p. 28.
Hino et al., Journal of Antibiotics, 38, 1985, pp. 926-935.

*Primary Examiner*—Mary C. Lee
*Assistant Examiner*—J. Richter
*Attorney, Agent, or Firm*—Finnegan, Henderson, Farabow, Garrett & Dunner

[57] ABSTRACT

Heterocyclic sulfides of the general formula heterocycle-S-R, a process for their preparation and, in particular, their use for immunostimulation, immunorestoration and cytostatic treatment, and pharmaceutical agents, which contain a sulfide of this type, for these indications.

18 Claims, No Drawings

1,3-THIAZOLES AND THEIR USE AS IMMUNOMODULATORS

It is known that the defense mechanisms of the living body, which are briefly termed the humoral immunity and cellular immunity, cooperate to neutralize and eliminate foreign bodies which may give rise to pathogenetic changes and be injurious, principally microorganisms or neoplastic cells.

Immunological investigations have shown that there are connections between a decrease in immunological activity provoked by internal or external factors and an increase in the infectious or tumorous diseases. In addition, other diseases arise owing to changes in the functioning of the immune system. These include, for example, autoimmune diseases or disorders caused by immune complexes. Thus, there has for a long time been a search for immunostimulants, that is to say substances which are able to modify the immunological activity of the recipient, preferably to increase it, and which allow, by reason of their high efficacy and good tolerability, wide use to support the body's defenses. Examples which have been tested for their stimulation of immunity are BCG and C. parvum, as well as extracts of M. tuberculosis and of the brucellae.

However, at the concentrations at which these substances are used they produce marked side effects such as, for example, local granulomas to varying extents. The lack of knowledge of the exact nature of these substances makes it difficult to carry out a systematic investigation with reasonable reproducibility of the clinical results. Thus, in this connection there is a requirement for new immunostimulants which are chemically defined substances and have low toxicity, such as, for example, bestatin which is an immunostimulant of low molecular weight undergoing intensive investigation at present and is, in general, a scientific reference substance.

It has now been found, surprisingly, that the compounds according to the invention have a potent immunostimulating and immunorestorative action, as is expressed, for example, in the DTH reaction on sheep erythrocytes, in the activation of mononuclear phagocytes and in a pronounced CSF activity. These immunostimulating effects can also be observed, for example, in an increase in the power of resistance to infections. Furthermore, the compounds according to the invention have, surprisingly, cytostatic activity, for example against B16 melanoma of the mouse.

The present invention thus describes a class of substances which have immunopharmacological and cytostatic activity, are chemically defined, have low toxicity and are, as such or combined with other active compounds, valuable medicaments. The compounds according to the invention have a LD$_{50}$ value above 1,000 mg/kg on intravenous injection in mice. The effective immunomodulatory and cytostatic amount for vertebrates, preferably warm-blooded mammals is in the range from about 0.5 to about 100 mg/kg of body weight for each parenteral or oral dose, and this shows no toxic side effects and is thus very well suited for the treatment of diseases of the immune system.

Thus the present invention relates to the use of compounds of the general formula I Het—S—R$^1$       (I)

for immunostimulation, immunorestoration and cytostatic treatment and to the use of these compounds for the preparation of a medicament to be used for this purpose.

The invention also relates to pharmaceutical agents for immunostimulation, immunorestoration and cytostatic treatment, which contain a compound of the formula I, and to the use of a pharmaceutical agent of this type for the medical indication mentioned.

In the compounds of the general formula I, Het represents an optionally substituted 5- or 6-membered heterocycle, and R$^1$ represents optionally substituted alkyl, alkenyl and alkynyl, whose chains can also be interrupted by heteroatoms, such as O, S or $$\begin{array}{c} R' \\ | \\ -N- \end{array},$$

R' denoting alkyl having 1–4 carbon atoms, and represents optionally substituted cycloalkyl. The heterocycle can contain, for example, 1 to 4 heteroatoms, in particular N, where appropriate in combination with S or O.

The following fundamental ring systems may be mentioned as examples of Het: thienyl, furyl, imidazolyl, pyrazolyl, thiazolyl, isothiazolyl, oxazolyl, isoxazolyl, triazolyl, thiadiazolyl, oxadiazolyl, tetrazolyl, pyridyl, pyrazinyl, pyrimidinyl, pyridazinyl, triazinyl and benzo-fused derivatives, such as benzoxazolyl, benzothiazolyl and benzimidazolyl, it also being possible for the ring systems to be entirely or partially hydrogenated, such as, for example, dihydrotriazinyl.

The preferred ring systems have 5 members and one sulfur or oxygen atom and 1 or 2 nitrogen atoms, such as thiazolyl, in particular 2-thiazolyl and 5-thiazolyl, 1,2,4-thiadiazolyl and 1,3,4-thiadiazolyl, in particular 1,3,4-thiadiazol-5-yl, oxadiazolyl, such as 1,3,4-oxadiazol-5-yl. Other preferred ring systems have 5 members and 1 to 4, in particular 2 to 4, nitrogen atoms such as, for example, imidazolyl, preferably 2-imidazolyl, triazolyl, preferably 1,3,4-triazol-5-yl and 1,2,4-triazol-5-yl. Benzo-fused derivatives are also preferred, in particular benzoxazol-2-yl, benzothiazol-2-yl and benzimidazol-2-yl.

Other suitable and preferred ring systems have 6 members and 1 to 3, preferably 1 or 2 nitrogen atoms, such as, for example, pyridyl, preferably 2-pyridyl, 3-pyridyl and 4-pyridyl, pyrimidyl, preferably 2-pyrimidyl and 4-pyrimidyl, triazinyl, preferably 1,2,4-triazin-3-yl, and 2,5- and 4,5-dihydro-1,2,4-triazin-3-yl. The Het radical can be substituted, examples of suitable substituents being the following:

The Het radical can be substituted, examples of suitable substituents being the following:

Straight-chain and branched alkyl groups having 1–6, preferably 1–4 carbon atoms, such as, for example, methyl, ethyl, n- or i-propyl, n- or tert.-butyl, preferably methyl, which can, where appropriate, in turn be substituted by halogen, such as, for example; chlorine or bromine, hydroxyl, alkoxy having 1–4 carbon atoms, such as, for example, methoxy or ethoxy, amino, alkylamino or dialkylamino having 1–4 carbon atoms in each alkyl radical, such as, for example, methylamino, ethylamino, dimethylamino and diethylamino, mercapto, alkylthio having 1–4 carbon atoms, such as, for example, methylthio and ethylthio, alkoxycarbonyl having 1–4 carbon atoms in the alkyl moiety, such as, for example, methoxycarbonyl and ethoxycarbonyl, aminocarbonyl, N-alkylaminocarbonyl or N,N-dialkylaminocarbonyl having 1–4 carbon atoms in each alkyl moiety, such as, for example, N-methylaminocarbonyl and N-ethylaminocarbonyl or N,N-dimethylaminocarbonyl and N,N-diethylaminocarbonyl, carboxyl, sulfo, phospho, 1H-tetrazol-5-yl, aryl, such as, for example, phenyl, halogen, such as, for example, chlorine or bromine, hydroxyl, oxo, oxido, alkoxy having 1–4 carbon atoms, such as, for example, methoxy or ethoxy, amino, alkylamino or dialkylamino having 1–4 carbon atoms in each alkyl moiety, such as, for example, methylamino, ethylamino, dimethylamino and diethylamino, or acylamino, it being possible for acyl to represent the radical of an aliphatic mono- or dicarboxylic acid having 2–5 carbon atoms, such as for example, acetyl, propionyl, 3-carboxy-propionyl, 4-carboxybutyryl, preferably acetyl, alkylthio, alkenylthio and alkynylthio having 1–4 carbon atoms in the alkyl moiety and 2–4 carbon atoms in the alkenyl and alkynyl moiety, such as, for example, methylthio, ethylthio, vinylthio, allylthio, ethynylthio or propynylthio, which can optionally be substituted by carboxyl, sulfo, phospho, 1H-tetrazol-5-yl or aminocarbonyl, alkenyl having 2–4 carbon atoms, such as, for example, vinyl or allyl, which can be optionally substituted by halogen such as, for example, chlorine or bromine, hydroxyl, alkoxy having 1–4 carbon atoms, such as, for example, methoxy or ethoxy, alkoxycarbonyl having 1–4 carbon atoms in the alkyl moiety, such as, for example, methoxycarbonyl or ethoxycarbonyl, aminocarbonyl, N-alkylaminocarbonyl, N,N-dialkylaminocarbonyl having 1–4 carbon atoms in each alkyl moiety, such as, for example, N-methylaminocarbonyl and N-ethylaminocarbonyl or N,N-dimethylaminocarbonyl and N,N-diethylaminocarbonyl, carboxyl, sulfo, phospho, 1H-tetrazol-5-yl, carboxyl or alkoxycarbonyl having 1–4 carbon atoms in the alkyl moiety, such as, for example, methoxycarbonyl or ethoxycarbonyl.

If $R^1$ denotes an alkyl radical, then straight-chain and branched alkyl preferably having 1–6 carbon atoms, and cycloalkyl preferably having 3–6 carbon atoms are suitable for this, such as, for example, methyl, ethyl, n- and i-propyl, n-butyl, n-pentyl, n-hexyl, cyclopropyl, cyclobutyl, cyclopentyl and cyclohexyl, which can optionally be substituted by amino, hydroxyl, in particular carboxyl and alkoxycarbonyl having 1–4 carbon atoms in the alkyl moiety, such as methoxycarbonyl and ethoxycarbonyl, by alkoxy having 1–4 carbon atoms, such as, in particular, methoxy, by aminocarbonyl, by oximino and alkoximino having 1–4 carbon atoms, such as, in particular, methoximino, and by phenyl which can optionally be substituted once to 3 times, preferably once, by alkyl having 1–4 carbon atoms, such as, in particular, methyl, carboxyl, aminocarbonyl, alkoxycarbonyl having 1–4 carbon atoms in the alkyl moiety, such as, in particular, methoxycarbonyl and ethoxycarbonyl, and halogen such as, in particular, fluorine, chlorine and bromine.

If $R^1$ denotes alkenyl or alkynyl, then straight-chain and branched alkenyl or alkynyl preferably having 2–6, in particular 2–4, carbon atoms is suitable for this, such as, in particular, vinyl, 1-propenyl, 3-propenyl, 2-butenyl, 1-propynyl and 3-propynyl, which can optionally be substituted by amino, hydroxyl, in particular carboxyl and alkoxycarbonyl having 1–4 carbon atoms in the alkyl moiety, such as methoxycarbonyl and ethoxycarbonyl, by alkoxy having 1–4 carbon atoms, such as, in particular, methoxy, by aminocarbonyl, and by phenyl which can optionally be substituted once to 3 times, preferably once, by alkyl having 1–4 carbon atoms, such as, in particular, methyl, carboxyl, aminocarbonyl, alkoxycarbonyl having 1–4 carbon atoms in the alkyl moiety, such as, in particular, methoxycarbonyl and ethoxycarbonyl, and halogen, such as, in particular, fluorine, chlorine and bromine.

Within the general formula I, the use according to the invention also covers new compounds.

Accordingly, the present invention also relates to new low-molecular weight sulfides of the formula II $$R^2-S-Het' \qquad (ii)$$

in which Het' represents a 5-membered ring system having one sulfur and 1 or 2 nitrogen atoms or having 1–3 nitrogen atoms, such as, for example, thiazolyl, in particular 2-thiazolyl and 5-thiazolyl, 1,3,4-thiadiazolyl, in particular 1,3,4-thiadiazol-5-yl, imidazolyl, in particular 2-imidazolyl, and triazolyl, in particular 1,2,4-triazol-5-yl. Benzo-fused derivatives are also preferred, in particular benzothiazol-2-yl and benzimidazol-2-yl.

Het' can also represent a 6-membered ring having 1–3 nitrogen atoms, such as, for example, pyridyl, in particular 2-pyridyl, pyrimidyl, in particular 2-pyrimidyl, and triazinyl, in particular 1,2,4-triazin-3-yl, it also being possible for the ring systems to be entirely or partially hydrogenated, such as, for example, dihydrotriazinyl.

The heterocyclic radical can be substituted, examples of suitable substituents being the following:

Straight-chain and branched alkyl groups having 1–6 carbon atoms, optionally substituted by hydroxyl, alkoxy having 1–4 carbon atoms, such as, for example, methoxy, ethoxy, amino, alkylamino or dialkylamino having 1–4 carbon atoms in each alkyl radical, such as, for example, methylamino, ethylamino, dimethylamino and diethylamino, mercapto, alkylthio having 1–4 carbon atoms, such as, for example, methylthio and ethylthio, alkoxycarbonyl having 1–4 carbon atoms in the alkyl moiety, such as, for example, methoxycarbonyl and ethoxycarbonyl, aminocarbonyl, N-alkylaminocarbonyl or N,N-dialkylaminocarbonyl having 1–4 carbon atoms in each alkyl moiety, such as, for example, N-methylaminocarbonyl, N-ethylaminocarbonyl or N,N-dimethylaminocarbonyl or N,N-diethylaminocarbonyl, carboxyl, aryl such as, for example, phenyl, hydroxyl, oxo, oxido, alkoxy having 1–4 carbon atoms, such as, for example, methoxy or ethoxy, amino, alkylamino or dialkylamino having 1–4 carbon atoms in each alkyl moiety, such as, for example, methylamino, ethylamino, dimethylamino or diethylamino, or acylamino, it being possible for acyl to represent the radical of an aliphatic mono- or dicarboxylic acid having 2–5 carbon atoms, such as, for example, acetyl, propionyl, 3-carboxypropionyl and 4-carboxybutyryl, preferably acetyl, alkenyl having 2–4 carbon atoms, such as, for example, vinyl and allyl, optionally substituted by alkoxy having 1–4 carbon atoms in the alkyl moiety, such as, for example, methoxy and ethoxy, alkoxycarbonyl having 1–4 carbon atoms in the alkyl moiety, such as, for example, methoxycarbonyl and ethoxycarbonyl, aminocarbonyl, N-alkylaminocarbonyl, N,N-dialkylaminocarbonyl having 1–4 carbon atoms in each alkyl moiety, such as, for example, N-methylaminocarbonyl, N-ethylaminocarbonyl or N,N-dimethylaminocarbonyl and N,N-diethylaminocarbonyl, and carboxyl, carboxyl, or alkoxycarbonyl having 1–4 carbon atoms in the alkyl moiety, such as, for example, methoxycarbonyl and ethoxycarbonyl.

$R^2$ represents an optionally substituted alkyl, alkenyl, alkynyl or cycloalkyl radical.

If $R^2$ denotes an alkyl or cycloalkyl radical, then straight-chain and branched alkyl preferably having 1–6 carbon atoms, and cycloalkyl preferably having 3–6 carbon atoms, are suitable for this, such as, for example, methyl, ethyl, n-propyl, i-propyl, n-butyl, n-pentyl, n-hexyl, cyclopropyl, cyclobutyl, cyclopentyl and cyclohexyl, which can optionally be substituted once or several times by amino, hydroxyl, in particular carboxyl and alkoxy-carbonyl having 1–4 carbon atoms in the alkyl moiety, such as methoxycarbonyl and ethoxycarbonyl, by alkoxy having 1–4 carbon atoms, such as, in particular, methoxy, by aminocarbonyl, by oximino and alkoximino having 1–4 carbon atoms, such as, in particular, methoximino, and by phenyl which can optionally be substituted once to three times, preferably once, by alkyl having 1–4 4 carbon atoms, such as, in particular, methyl, carboxyl, aminocarbonyl, alkoxycarbonyl having 1–4 carbon atoms in the alkyl moiety, such as, in particular, methoxycarbonyl and ethoxycarbonyl, and halogen such as, in particular, fluorine, chlorine and bromine.

If $R^2$ denotes alkenyl or alkynyl, then straight-chain and branched alkenyl or alkynyl preferably having 2–6, in particular 2–3, carbon atoms is suitable for this, such as, in particular, vinyl, 1-propenyl, 3-propenyl, 2-butenyl, 1-propynyl and 3-propynyl, which can optionally be substituted by amino, hydroxyl, in particular carboxyl and alkoxycarbonyl having 1–4 carbon atoms in the alkyl moiety, such as methoxycarbonyl and ethoxycarbonyl, by alkoxy having 1–4 carbon atoms, such as, in particular, methoxy, by aminocarbonyl, and by phenyl which can optionally be substituted once to 3 times, preferably once, by alkyl having 1–4 carbon atoms, such as, in particular, methyl, carboxyl, aminocarbonyl, alkoxycarbonyl having 1–4 carbon atoms in the alkyl moiety, such as, in particular, methoxycarbonyl and ethoxycarbonyl, and halogen, such as, in particular, fluorine, chlorine and bromine.

If the radical $R^1$ or $R^2$ in the meaning of an alkyl, alkenyl or alkynyl radical is substituted, then particularly preferred substituents which may be mentioned are hydroxyl, carboxyl, methoxy, aminocarbonyl, and phenyl which in turn can be substituted, particularly preferably by carboxyl and aminocarbonyl.

The heterocycles Het and Het' can be substituted once or several times, for example 1–3 times, in the manner described above. However, preference is given to heterocycles Het and Het' which carry one or 2 substituents in the heterocyclic ring or in the carbocyclic ring which is fused on. Those which are particularly preferred are ones in which at least one of these substituents carries an acid group, in particular a carboxyl group such as, for example, carboxyalkyl or carboxyalkylthio.

Preference is also given to heterocycles Het and Het' which carry in the heterocyclic moiety or in the fused-on carbocyclic ring one or two substituents, at least one of which is a directly bonded acid group such as, for example, carboxyl or hydroxyl.

If the substituents on the heterocycle Het and Het', such as, for example, alkyl, alkenyl, alkylthio, alkenylthio or alkynylthio, are further substituted in the manner described above, then they can also carry more than one substituent, for example 1–3 other substituents. However, single substitution is preferred.

If $R^1$ and $R^2$ are substituted in the manner described above, then they can be substituted once or several times, for example once to three times. However, substitution once or twice, in particular once, is preferred.

Of very special interest according to the invention are compounds of the general formula

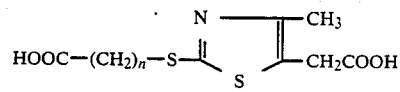

in which n can be 1–5, and within this group the compound in which n is 3 occupies a particularly preferred position.

Where the compounds of the formulae I or II carry acid groups they can also be in the form of their physiologically tolerated salts, for example as alkali metal and alkaline earth metal salts such as, preferably, the Na, K, Ca or Mg salts or, for example, ammonium salts or substituted ammonium salts such as, for example, $NH_4+$, ethanolammonium, diethanolammonium, trialkylammonium, such as, for example, triethylammonium, tetraalkylammonium, or salts with basic amino acids such as, for example, lysine or arginine.

The invention also relates to processes for the preparation of the compounds of the formula II according to the invention. If $R^2$ and Het' in formula II represent the abovementioned meanings, then the preparation process comprises reaction of a heterocyclic thio compound of the general formula III

in which Het' has the abovementioned meaning, with an alkylating agent of the formula IV

in which $R^2$ has the abovementioned meaning, and conversion, where appropriate, of the abovementioned substituents, according to the invention, of Het' and/or $R^2$ into others of the abovementioned substituents, according to the invention, of Het' and/or $R^2$.

It is also possible to prepare the compounds of the formula II, according to the invention, by reaction of a heterocyclic compound of the formula V

in which Het' has the abovementioned meaning, with a thiol compound of the formula VI

in which $R^2$ has the abovementioned meaning, and conversion, where appropriate, of the abovementioned substituents, according to the invention, of Het' and/or $R^2$ into others of the abovementioned substituents, according to the invention, of Het' and/or $R^2$.

X in formulae IV and V represents a readily replaceable group such as, for example, halogen, preferably chlorine, bromine and iodine, or $OSO_2R^3$, $R^3$ representing $C_1$-$C_4$-alkyl such as, preferably, methyl, halogeno-$C_1$-$C_4$-alkyl such as, preferably, trifluoromethyl, or optionally substituted phenyl such as, preferably, phenyl or p-tolyl.

It is quite generally possible to convert, by processes known from the literature, the substituents contained in R[2] and/or Het' in the sulfides of the formula II into other substituents according to the invention. Thus, for example, an alkoxycarbonyl or aminocarbonyl group can be converted by hydrolysis, or in the case of the aminocarbonyl group also by nitrosation, into a free carboxyl group.

The reaction can be carried out in aqueous solution, in an organic solvent such as, for example, alcohol, in particular a low molecular weight alcohol, for example methanol, ethanol, propanol or isopropanol, in an ether such as, for example, diethyl ether, tetrahydrofuran or dioxane, in dimethylformamide, dimethylacetamide, acetone, methyl ethyl ketone, acetonitrile, ethyl acetate or in a mixture of the solvents mentioned. It may be appropriate to carry out the reaction in a 2-phase system of water and a solvent which is immiscible or only partly miscible with water, such as, for example, ethyl acetate, diethyl ether, methylene chloride, chloroform or toluene.

Examples of preferred solvents which may be mentioned are water, methanol, ethanol, acetone, dimethylformamide, dimethylacetamide, tetrahydrofuran and dioxane.

It may be necessary, for speeding up the preparation methods mentioned, to add a basic substance in an amount which is equimolar or up to ten molar, such as, for example, sodium hydroxide, potassium hydroxide, sodium carbonate, potassium carbonate, sodium bicarbonate or potassium bicarbonate. It is also possible to use organic bases such as, for example, amines, preferably diethylamine, triethylamine, diisopropylamine, ethyldiisopropylamine, N,N-dimethylaniline, pyridine, piperidine, N,N'-dimethylpiperidine, morpholine or N-methylmorpholine.

If the reaction is carried out in a two-phase system, then it may be advantageous to add a phase-transfer catalyst such as, for example, quaternary ammonium salts such as, preferably, tetrabutylammonium chloride, tetrabutylammonium bromide, tetrabutylammonium iodide, tetrabutylammonium bisulfate, benzyltrimethylammonium bromide or benzyldimethyl-n-dodecylammonium bromide, or tertiary phosphonium compounds such as, for example, ethyltrioctylphosphonium bromide and hexadecyltributylphosphonium bromide.

The reaction can be carried out in a temperature range between about $-20°$ C. and the boiling point of the solvent used, or that of the solvent mixture, preferably between about $+5°$ C. and the boiling point.

The active compound can be administered alone as well as combined with one or more, preferably with one other, medicament which has a favorable effect on infections which are caused by, for example, bacteria, fungi or viruses, and on tumorous diseases. According to the invention, the active compounds can be administered both parenterally and orally. Suitable for parenteral administration are solutions or suspensions of the active compound in a pharmaceutically tolerated vector, preferably a vegetable oil such as, for example, peanut oil or sesame oil, and alcoholic solutions of the active compound, for example, in ethanol, propanediol or glycerol or in mixtures of the abovementioned solvents. To prepare aqueous solutions, the active compound is preferably used in the form of physiologically tolerated salts which are soluble in water. It is possible for the formulations to contain the customary auxiliaries and excipients. Examples of these are fillers, emulsifiers, lubricants and buffers and flavor-modifying agents.

In the text which follows, the action of the compounds on the immune response of the mouse and their immunostimulant activities in various in vivo standard methods are illustrated by way of example. The various test methods employed are known to be particularly well suited for the assessment of immunostimulants and their quality of action.

EXPERIMENT 1

Effect On The Cellular Immunological Reaction, of the Delayed Type, to Sheep Erythrocytes (Delayed Type Hypersensitivity, DTH)

Either $10^6$ or $10^9$ red blood cells from sheep were administered intravenously to each animal in groups of 5 female NMRI mice weighing 18–20 g. Sheep erythrocytes are regarded in immunology as a standard test substance (antigen) for the induction of cellular and humoral immune reactions. In particular, this test provides information about the functioning of the T-cell-dependent component (T-helper cells) of the immune system. The test substance obtained as in exemplary embodiment 7 ([2-(3-carboxy-1-propylthio)-4-methyl-1,3-thiazol-5-yl]acetic acid) was administered intraperitoneally and perorally, respectively, in the concentrations 10–100 mg/kg in physiological saline solution on days -3, -2, -1 and 0. After 5 days, each animal received $2 \times 10^8$ sheep erythrocytes injected into the underside of the foot and, 24 hours later, the swelling of the foot was measured. The foot swelling is induced by a skin reaction of the delayed type (delayed type hypersensitivity, DTH) and is, as is known to the expert, a measure of the cellular immune response (Collins, F. M. and Mackaness, G. B., J. Immunol. 101, 830–845, 1968). The results compiled in Table 1 illustraste that there is an increase in the cellular immune response owing to the administration of the subst nce obtained according to the invention, for example after imnunization with $10^6$ or $10^9$ sheep erythrocytes. An optimum stimulation can be observed in this experimental design on administration of 20–40 mg/kg test substance.

TABLE 1

Immunization of mice with sheep erythrocytes - action on the cellular immune response (DTH reaction).

| 1 ×/day i.p. administration on days −3, −2, −1 and 0 of | % foot swelling with $10^9$ erythrocytes |
|---|---|
| PBS* | 15.1 ∓ 4.2 |
| Test substance 10 mg/kg | 23.5 ∓ 2.8 |
| Test substance 20 mg/kg | 27.8 ∓ 3.7 |
| Test substance 40 mg/kg | 26.3 ∓ 2.5 |
| Test substance 60 mg/kg | 23.8 ∓ 5.7 |
| Test substance 80 mg/kg | 20.8 ∓ 3.5 |
| Test substance 100 mg/kg | 18.2 ∓ 2.7 |
| 1 ×/day p.o. administration on day −3, −2, −1 and 0 of | $10^6$ erythrocytes |
| PBS | 17.9 ∓ 3.2 |
| Test substance 10 mg/kg | 24.4 ∓ 6.2 |
| Test substance 20 mg/kg | 27.9 ∓ 8.8 |
| Test substance 40 mg/kg | 43.5 ∓ 10.5 |
| Test substance 60 mg/kg | 26.8 ∓ 4.4 |
| Test substance 80 mg/kg | 25.3 ∓ 3.5 |
| Test substance 100 mg/kg | 23.2 ∓ 6.5 |

*PBS = phosphate-buffered saline (NaCl: 8,000 mg/l; KCl: 200 mg/l, Na$_2$HPO$_4$.2-H$_2$O: 1,440 mg/l, KH$_2$PO$_4$: 200 mg/l)

EXPERIMENT 2

Effect on the Stimulation of Non-Specific Immunity Activation of Mononuclear Phagocytes This entailed investigation of the effect of the test substance obtained as in exemplary embodiment 7 on the stimulation of peritoneal macrophages in 6–8 week old NMRI mice. Female mice received the test substance in parenteral or oral doses of 25 mg/kg, 50 mg/kg, 100 mg/kg and 200 mg/kg. Buffered saline solution was administered to a control group. The mice were sacrificed three days after the injections, and the peritoneal macrophages of the animals were examined for their state of activation. The secretion of the lysosomal enzymes ($\beta$-galactosidase, $\beta$-glucuronidase and N-acetyl-$\beta$-D-glucosaminidase) was determined as one measure of macrophage activation. In addition, it was possible to examine the pinocytosis in comparable macrophage cultures by the uptake of colloidal gold ($^{198}$Au) -as is known to the expert. The level of oxidative metabolism in macrophages is taken as another measure of their state of activation. This activity is measured with the assistance of a biolumate by determination of the chemiluminescence.

For this purpose, either $3 \times 10^6$ macrophages were cultured with 1 ml of TC 199 culture medium in Petri dishes of diameter 30 mm or $10^6$ macrophages were cultured with 100 $\mu$l of medium in round-bottomed polyethylene tubes (for determination of the chemiluminescence), with 5% $CO_2$ and at 37° C.

After incubation for one hour, the cultures were washed to remove floating cells. The chemiluminescence (tube culture) was then determined directly, whereas the Petri dishes were incubated for a further 24 hours at 37° C. and then the enzyme and pinocytosis activities in the cultures were determined. The following results were obtained.

TABLE 2

| Action on the oxidative metabolism in mouse peritoneal macrophages (chemiluminescence in RLU*/15 minutes). | | |
|---|---|---|
| 1 × administration | i.p. | p.o. |
| PBS | $3.09 \mp 0.12 \times 10^5$ | $1.86 \mp 0.09 \times 10^5$ |
| Test substance 25 mg/kg | $34.17 \mp 0.16 \times 10^5$ | $31.28 \mp 0.18 \times 10^5$ |
| 50 mg/kg | $86.42 \mp 0.68 \times 10^5$ | $47.24 \mp 0.36 \times 10^5$ |
| 100 mg/kg | $143.37 \mp 0.82 \times 10^5$ | $80.41 \mp 0.72 \times 10^5$ |
| 200 mg/kg | $162.04 \mp 1.19 \times 10^5$ | $115.52 \mp 1.44 \times 10^5$ |

*RLU = relative light units

Both parenteral and oral treatment of NMRI mice with the test substance prepared as in Example 7 stimulate macrophage activity and thus have an immunity-stimulating action. Thus, the oxidative metabolism of macrophages, with the generation of oxygen radicals and the measurable light associated with this, is markedly raised. At dosages of 25 mg/kg upwards, there is a dose-dependent increase in the macrophage activity with both parenteral and oral administration.

It can be seen from Table 3 that macrophages from control mice release only small amounts of lysosomal enzymes ($\beta$-glucuronidase, $\beta$-galactosidase and N-acetyl-$\beta$-D-glucosaminidase) into the culture supernatant. Mononuclear phagocytes from mice which have been treated parenterally or orally with the test substance for 72 hours secrete markedly more of the abovementioned acid hydrolases ($\beta$-Glu, $\beta$-Gal and N-Ac-Glu), and thus show a dose-effect curve which demonstrates a superiority over the controls for all the enzymes measured. It is evident that the test substance has a stimulant action on macrophage activity and contributes to an increase in enzyme release.

TABLE 3

| Effect of the test substance on the release of the lysosomal hydrolase enzymes from mouse peritoneal macrophages. | | | | |
|---|---|---|---|---|
| 1 × i.p./p.o. administration | | N—Ac—Glu % release | $\beta$-Glu % release | $\beta$-Gal % release |
| PBS | | 7.5/ 6.8 | 13.5/16.4 | 14.9/12.6 |
| Test substance | 25 mg/kg | 17.2/15.4 | 20.0/17.5 | 24.1/20.4 |
| | 50 mg/kg | 26.0/22.8 | 30.9/25.1 | 33.5/26.9 |
| | 100 mg/kg | 40.8/37.3 | 42.8/38.2 | 52.9/43.6 |
| | 200 mg/kg | 51.5/45.2 | 58.2/49.8 | 65.4/54.8 |

The quantitative determination of the pinocytosis activity of mononuclear phagocytes was carried out by the method of Davies et al. (Davies, P., Allison, A. C. and Haswell, A. D.; Biochem. Biophys. Res. Com. 52, 627, 1973). Radioactive colloidal gold ($^{198}$Au) with a particle size of 20 nm and a specific activity of 4–12 mCi/mg of Au was used for this. The results in Table 4 illustrate the effect of the test substance obtained as in Example 7 on the efficiency of endocytosis. The pinocytosis of colloidal gold ($^{198}$Au) by mouse peritoneal macrophages from animals treated with the compound according to the invention is significantly and dose-dependently higher than by macrophages from untreated animals.

TABLE 4

| The effect of the test substance on the efficiency of pinocytosis of mouse macrophages. | | |
|---|---|---|
| 1 × administration of | intraperitoneal | oral |
| PBS | $0.201 \times 10^3$ cpm | $0.150 \times 10^3$ cpm |
| Test substance 25 mg/kg | $0.415 \times 10^3$ cpm | $0.365 \times 10^3$ cpm |
| 50 mg/kg | $0.558 \times 10^3$ cpm | $0.448 \times 10^3$ cpm |
| 100 mg/kg | $0.718 \times 10^3$ cpm | $0.661 \times 10^3$ cpm |
| 200 mg/kg | $0.862 \times 10^3$ cpm | $0.739 \times 10^3$ cpm |

EXPERIMENT 3

Increase in the Resistance of Balb/c Mice to Infection with *Candida albicans*

(a) Therapeutic treatment

For the therapeutic treatment of chronic *Candida albicans* infection, female Balb/c mice (16/group) were infected intravenously with *Candida albicans* ($2.5 \times 10^5$ cfu/mouse) (day 0). After the infection had taken place, the animals were treated intraperitoneally on 13 consecutive days (days 3–15) with the test substance obtained as in Example 7; the concentrations were 0.5, 2.0, 5.0, 10.0, 30.0 and 60.0 mg/kg. The control animals received administrations of physiological saline solution. Urine was collected from the animals on days 19 and 24, and the organism count was determined. On day 26, the animals were sacrificed, and the organism count and the necroses in the kidneys were determined.

Table 5 shows that there was a reduction at all concentrations of the test substance in the organism counts in the urine and kidneys and in the formation of necroses in the kidneys. The optimal action was observed at 0.5–5.0 mg/kg. Thus, a marked improvement in the course of a chronic infection can be achieved by therapeutic administration of the substance.

TABLE 5

Therapy of a chronic Candida albicans infection

| Group | | Kidneys infected with C. albicans (%) | Ne-crotic kidneys (%) | Urine infected with C. albicans d19 (%) | d24 (%) |
|---|---|---|---|---|---|
| Control | | 66 | 75 | 38 | 53 |
| Test | 0.5 mg/kg | 27 | 27 | 0 | 6 |
| sub- | 2.0 mg/kg | 13 | 7 | 6 | 6 |
| stance | 5.0 mg/kg | 27 | 47 | 0 | 7 |
| | 10.0 mg/kg | 29 | 43 | 7 | 21 |
| | 60.0 mg/kg | 38 | 31 | 13 | 13 |

Days 3–15
10 × i.p.

(b) Combination therapy with an antimycotic

In this experiment, the test substance obtained as in Example 7 was used together with the antimycotic ketoconazole (Nizoral ®, Janssen). Female Balb/c mice (15/group) were infected intravenously with Candida albicans ($10^6$ cfu/mouse) (day 0). Three groups were formed: group 1 was treated with physiological saline solution, and group 2 received 70 mg/kg ketoconazole orally on 7 consecutive days (days −1–6). Group 3 received 10 intraperitoneal injections of 2 mg/kg test substance on days 3–30 (every 3rd day) in addition to ketoconazole. The number of animals which died was recorded each day, and the time at which 50% of the animals in each group had died ($T_{50}$) was determined. Table 6 shows that the animals which received a combination of ketoconazole and the test substance had a markedly higher survival time ($T_{50}$) than the animals which received ketoconazole alone.

TABLE 6

Combination of the test substance with an antimycotic.
$T_{50}$ values in days

| Group | $T_{50}$ |
|---|---|
| 1. Control | 8 |
| 2. Ketoconazole 70 mg/kg (d-1-6- p.o.) | 18 |
| 3. Ketoconazole 70 mg/kg (d-1-6 p.o.) + test substance 2 mg/kg (10 × i.p., d3-30, every 3rd day) | 30 |

EXPERIMENT 4

Stimulation of the DTH Reaction by the Compounds According to the Invention

NMRI mice were treated with the substances according to the invention as described in experiment 1.

The DTH reaction was checked as a test to determine the immunostimulation.

Table 7 shows the relative activity of the test substances, related to the compound from Example 7 whose maximal activation corresponds to 100% (difference between control and stimulation). It can be seen from the table that the DTH reaction in the animals pretreated with the test substances is more pronounced than in the corresponding control animals.

TABLE 7

| Compound from Example No. | Dose (mg/kg) | Administration | DTH reaction (SRBC) |
|---|---|---|---|
| 7 | 200 | 1 × i.p. day 0 | 100% |
| 24 | 100 | 1 × i.p. day 0 | 115% |
| 25 | 100 | 1 × i.p. day 0 | 115% |

TABLE 7-continued

| Compound from Example No. | Dose (mg/kg) | Administration | DTH reaction (SRBC) |
|---|---|---|---|
| 27 | 20 | 1 × i.p. day 0 | 144% |
| 39 | 100 | 1 × i.p. day 0 | 210% |

EXPERIMENT 5

Stimulation of Macrophage Activity by the Compounds According to the Invention

NMRI mice were treated with the compounds according to the invention as described in experiment 2.

The macrophage function (chemiluminescence and enzyme activity) was checked as a test to determine the immunostimulation.

Table 8 shows the relative activity of the test substances, related to the compound from Example 7 whose maximal activation (difference between control and stimulation) corresponds to 100%. It can be seen from the table that in comparison with macrophages from untreated animals, the chemiluminescence reaction of these cells was also greatly stimulated by all the test substances, and their content of lysosomal enzymes was markedly raised.

TABLE 8

| Compound from Example No. (100 mg/kg i.p.) | Administration | Macrophage activity | |
|---|---|---|---|
| | | Chemi-luminescence | Exocytosis |
| 1 | 1 × i.p. day 0 | 29% | 124% |
| 7 | 1 × i.p. day 0 | 100% | 100% |
| 15 | 1 × i.p. day 0 | 49% | 172% |
| 24 | 1 × i.p. day 0 | 57% | 218% |
| 25 | 1 × i.p. day 0 | 26% | 186% |
| 27 | 1 × i.p. day 0 | 22% | 258% |
| 39 | 1 × i.p. day 0 | 35% | 148% |

EXPERIMENT 6

Effect on the Formation of Metastases of the B16 Melanoma

For the treatment of metastases of the B16 melanoma, a primary tumor was induced in female C57Bl/6 mice (10 animals/group) with $2 \times 10^5$ live B16 melanoma cells. After amputation of this tumor the B16 melanoma metastasizes into the lung, and the animals die. After tumor induction, the animals were treated intraperitoneally with 50 mg/kg of the test substance obtained as in Example 7, either on days 3, 5, 7, 9, 11 and 13 before or after amputation had taken place. The number of macroscopically detectable metastases in the lung was determined on days 14, 17, 21, 25 and 28 after amputation of the primary tumor had taken place.

As is evident from Table 9, the number of pulmonary metastases of the B16 melanoma was markedly less in the treated animal groups than in the corresponding control animals.

EXPERIMENT 7

TABLE 9

| | | Number of pulmonary metastases in the model of B16 melanoma | |
|---|---|---|---|
| | Control | Test substance (50 mg/kg, 6 × i.p.) | |
| Days up to counting of the metastases | 2 × 10⁵ tumor cells Number of metastases (death rate) | Days 3, 5, 7, 9, 11, 13 before amputation Number of metastases | Days 3, 5, 7, 9, 11, 13 after amputation Number of metastases |
| 14 | 13 ∓ 5 | 2 ∓ 2 | 6 ∓ 3 |
| 17 | 16 ∓ 3 | 5 ∓ 1 | 6 ∓ 4 |
| 21 | 22 ∓ 2 | 2 ∓ 2 | 5 ∓ 3 |
| 25 | 26 ∓ 2 (5/10) | 12 ∓ 5 | 6 ∓ 5 |
| 28 | 50 (9/10) | 15 ∓ 6 | 12 ∓ 3 |

Effect on Formation of Bone Marrow Colonies

This examined the effect of the test substance obtained as in Example 7 on the stimulation of bone marrow colonies in 6-8 week-old B2D2F1 mice. Female mice received the test substance intraperitoneally in the doses 2.5 and 5 mg/kg. The animals were sacrificed one day later, and the bone marrow cells were isolated and cultured by generally known methods (Metcalf, Immunology 21, 427, 1971 and Stanley et al., J. Exp. Med. 143, 631, 1979). As is customary, L-cell supernatant (15%) was used as CSF source (colony stimulating factor) for the development of the bone marrow colonies. The colonies were counted 8 days after the start of culturing. As can be seen in Table 10, a single dose of 2.5 or 5 mg of the test substance resulted in a marked increase in the formation of bone marrow cell colonies both with and without addition of CSF (colony stimulating factor) in vitro.

TABLE 10

| In vivo-effect on the formation of bone marrow colonies | | |
|---|---|---|
| Test substance | Number of bone marrow colonies (day 8) | |
| 1 × i.p. (mg/kg) | with CSF (15%) | without CSF (15%) |
| PBS | 77 ∓ 6 | 2 ∓ 1 |
| 2.5 | 134 ∓ 10 | 56 ∓ 4 |
| 5.0 | 217 ∓ 7 | 117 ∓ 11 |

The examples which follow illustrate the invention but do not restrict it.

EXAMPLE 1

Stage 1

Methyl 2-mercapto-4-methyl-1,3-thiazol-5-ylacetate 27.0 g (0.14 mole) of 2-mercapto-4-methyl-1,3-thiazol-5-ylacetic acid are dissolved in
230 ml of methanol, and 6 ml of concentrated HCl are added dropwise. The mixture is then stirred at room temperature for 4 h, and the precipitate is filtered off with suction and washed with a little methanol.
Yield 14.3 g = 49.3%.
A further 12.0 g = 41.4% are obtained from the mother liquor.
Melting point 134°-135° C.
NMR (d₆-DMSO) δ = 8.67 ppm s broad, 1H, —SH; 3.30 ppm s 2H CH₂—COOCH₃; 2.03 ppm s 3H 4—CH₃.

Stage 2

Methyl 2-methylmercapto-4-methyl-1,3-thiazol-5-ylacetate 28.0 g (0.14 mole) of stage 1 are dissolved in
500 ml of acetone and
38.1 g (0.28 mole) of finely ground potassium carbonate are added. After 10 minutes,
21.6 g = 9.5 ml (0.15 mole) of methyl iodide are added.

The temperature increases slightly. The mixture is then stirred at room temperature for 3 hours. The solid potassium iodide is filtered off with suction, and the filtrate is evaporated in a rotary evaporator. Residue 36.1 g of yellow oil = 100% of theory.
NMR (d₆-DMSO)δ = 3.50 ppm, s, 2H, —CH₂—COOCH₃; 3.30 ppm, s, 3H, CH₂—COOCH₃; 2.63 ppm, s, 3H, —S—CH₃; 2.23 ppm, s, 3H, 4—CH₃.

Stage 3

2-Methylmercapto-4-methyl-1,3-thiazol-5-ylacetic acid 36.1 g (0.166 mole) of compound from stage 2 are dissolved in
50 ml of methanol and
100 ml of 2N sodium hydroxide solution are added.

The mixture is boiled under reflux for one hour, the methanol is removed by distillation, and after the mixture has cooled it is extracted 2× with ethyl acetate. Acidification to pH 3 is carried out with concentrated hydrochloric acid, and the precipitate is filtered off with suction and recrystallized from isopropanol.
Yield 21.2 g = 62.9% of theory.
Melting point 159°-160° C.
IR. KBr (1870, 1710, 1550 cm⁻¹).
NMR (d₆-DMSO)δ = 3.73 ppm, s, 2H, CH₂—COOH; 2.63 ppm, s, 3H, S—CH₃; 2.20 ppm, s, 3H, 4—CH₃; 12.77 ppm, s, 1H, COOH.

EXAMPLE 2

Stage 1

Methyl 2-ethylmercapto-4-methyl-1,3-triazol-5-ylacetate 2.03 g (0.01 mole) of compound from Example 1, stage 1, are reacted with potassium carbonate and ethyl iodide and worked up in analogy to Example 1, stage 2.
Yield 2.8 g of oil.
NMR (d₆-DMSO)δ = 3.83 ppm, s, 2H, CH₂—CO₂CH₃; 3.63 ppm, s, 3H, COO—CH₃; 3.10 ppm, q, 2H, SCH₂CH₃; 2.23 ppm, s, 3H, 4CH₃; 1.33 ppm, t, 3H, S—CH₂CH₃.

Stage 2

2-Ethylmercapto-4-methyl-1,3-thiazol-5-ylacetic acid 2.8 g of compound from stage 1 are reacted and worked up in analogy to Example 1, stage 3.
Yield 1.1 g.
Melting point 124°-5° C.
NMR (d₆-DMSO)δ = 3.75 ppm, s, 2H, CH₂—COOH; 3.14 ppm, q, 2H, S—CH₂—CH₃; 2.23 ppm, s, 3H, 4CH₃; 1.33 ppm, tr, 3H, S—CH₂—CH₃.

EXAMPLE 3

Stage 1

Methyl 2-benzylmercapto-4-methyl-1,3-thiazol-5-ylacetate 2.03 g (0.01 mole) of methyl 2-mercapto-4-methyl-1,3thiazol-5-ylacetate are reacted with potassium carbonate and benzyl chloride in acetone and worked up in accordance with Example 1, stage 2.

Yield 3.3 g of oil, 100% of theory.

NMR (d$_6$-DMSO)$\delta$=7.27 ppm, d, 5H, aromat; 4.40 ppm, s, 2H, benzyl CH$_2$; 3.83 ppm, s, 2H, $\underline{CH_2}$—COOCH$_3$; 3.60 ppm, s, 3H, COOCH$_3$; 2.26 ppm, s, 3H, 4—CH$_3$.

Stage 2

2-Benzylmercapto-4-methyl-1,3-thiazol-5-ylacetic acid 3.03 g (0.01 mole) of compound from stage 1 are mixed with 2N sodium hydroxide solution in accordance with Example 1, stage 3, and worked up in accordance with the example specified.

Yield: 1.3 g.

Melting point 129°–130° C.

NMR (d$_6$-DMSO)$\delta$=7.36 ppm, d, 5H, phenyl; 4.43 ppm, s, 2H, benzyl CH$_2$; 3.75 ppm, s, 2H, CH$_2$—COOH; 2.28 ppm, s, 3H, 4—CH$_3$.

EXAMPLE 4

Methyl 2-n-propylmercapto-4-methyl-1,3-thiazol-5-ylacetate

Stage 1

2.03 g (0.01 mole) of compound from Example 1, stage 1, are reacted with potassium carbonate and n-propyl iodide in acetone in analogy to Example 1, stage 2, and worked up correspondingly.

Yield 3.9 g of oil, 100% of theory.

NMR (d$_6$-DMSO)$\delta$=3.83, s, 2H, $\underline{CH_2}$—COOCH$_3$; 3.62, s, 3H, COOCH$_3$; 3.10, t, 2H, CH$_2$—$\underline{CH_2}$ CH$_2$; 2.38, s, 3H, 4—CH$_3$; 1.67, q, 2H, CH$_2$—$\underline{CH_2}$—CH$_3$; 0.97, t, 3H, CH$_2$—CH$_2$—$\underline{CH_3}$.

Stage 2

2-n-Propylmercapto-4-methyl-1,3-thiazol-5-ylacetic acid 4.1 g (0.0168 mole) of compound from stage 1 are mixed with 2N sodium hydroxide solution in analogy to Example 1, stage 3, and worked up in accordance with Example 1, stage 3.

Yield 2.0 g=52% of theory.

Melting point 79°–80° C.

NMR (d$_6$-DMSO)$\delta$=12.60, br s, 1H, COOH; 3.73, s, 2H, $\underline{CH_2}$—COOH; 3.11, m, 2H, $\underline{CH_2}$—CH$_2$—CH$_3$; 2.20, s, 3H, 4CH$_3$; 1.70, q, 2H, CH$_2$—$\underline{CH_2}$—CH$_3$; 0.97, t, 3H, CH$_2$—CH$_2$—$\underline{CH_3}$.

EXAMPLE 5

(2-Carboxymethylthio-4-methyl-1,3-thiazol-5-yl)acetic acid 7.6 g of 2-mercapto-4-methyl-1,3-thiazol-5-ylacetic acid are dissolved in 50 ml of 2N sodium hydroxide solution, and 6.9 g of bromoacetic acid are added.

The mixture is heated on a steam bath for 3 h and, during this, the pH is maintained at 8 by adjustment with 2N NaOH. After the solution has been cooled it is filtered and acidified. 6.5 g of melting point 180° C. are obtained.

| Elemental analysis (C$_8$H$_9$NO$_4$S$_2$; 297.3) | | | | |
|---|---|---|---|---|
| calculated | C 38.8% | H 3.7% | N 5.7% | S 25.9% |
| found | 38.6% | 3.6% | 5.6% | 25.5% |

$^1$H-NMR (d$_6$-DMSO): $\delta$(ppm): 2.25 (s, CH$_3$-thiazole, 3H), 3.70 (s, 5-CH$_2$-thiazole, 2H), 3.93 (s, 2-CH$_2$-S-thiazole, 2H).

EXAMPLE 6

[2-(2-Carboxyethylthio)-4-methyl-1,3-thiazol-5-yl]acetic acid 3.14 g of 2-mercapto-4-methyl-1,3-thiazol-5-ylacetic acid are dissolved in 40 ml of N sodium hydroxide solution, and 2.16 g of 3-chloropropionic acid are added. After addition of a further 10 ml of N NaOH solution, the mixture is heated on a steam bath for 5 h.

The solution is acidified and cooled to complete crystallization. Filtration and recrystallization twice from ethyl acetate provided 2.5 g of melting point 124° C.

| Elemental analysis (C$_9$H$_{11}$NO$_4$S$_2$; 261.3) | | | |
|---|---|---|---|
| calculated | C 41.4% | H 4.2% | N 5.4% |
| found | 41.3% | 4.2% | 5.4% |

The hydrate can be obtained by recrystallization from water. 1.0 g provided 0.9 g of melting point 93° C.

| Elemental analysis (C$_9$H$_{11}$NO$_4$SO; 261.3 $\times$ H$_2$O; 279.3) | | | | |
|---|---|---|---|---|
| calculated | C 38.7% | H 4.7% | N 5.0% | S 22.9% |
| found | 39.2% | 4.8% | 4.9% | 23.1% |

$^1$H-NMR (d$_6$-DMSO):$\delta$(ppm) =2.17 (s, 4-CH$_3$-thiazole, 3H), 2.61 and 3.21 (2xt, J=7 Hz, —CH$_2$CH$_2$—, 4H), 3.72 (s, 4—CH$_2$-thiazole, 2H).

EXAMPLE 7

[2-(3-Carboxy-1-propylthio)-4-methyl-1,3-thiazol-5-yl]acetic acid

Stage 1

[2-(3-Methoxycarbonyl-1-propylthio)-4-methyl-1,3-thiazol-5-yl]acetic acid 9.27 g of 4-methoxybenzyl 2-mercapto-4-methyl-1,3-thiazol-5-ylacetate are dissolved in 100 ml of dry DMF, and 7.0 g of anhydrous, ground potassium carbonate are added.

4.5 g of methyl 4-chlorobutyrate are added dropwise to this suspension. The mixture is allowed to stir at room temperature for 6 h, and is filtered and the solvent is removed. The crude product is purified by chromatography on silica gel using ethyl acetate/cyclohexane (1:1). After removal of the solvent from the product fractions, it is dissolved in about 20 ml of methylene chloride, and 10 ml of trifluoroacetic acid are added. The mixture is allowed to stir at room temperature for 30 min, the solvent is removed in vacuo, and the residue is taken up in 100 ml of 2N sodium bicarbonate solution, which is extracted with ethyl acetate. The aqueous phase is acidified and again extracted with a total of 300 ml of ethyl acetate. The organic phases are dried with MgSO$_4$, and the solvent is removed. 3.5 g of stage 1 are obtained with a melting point of 80° C. after recrystallization from ethyl acetate/diisopropyl ether.

$^1$H—NMR (CDCl$_3$):
s, δ = 3.66; 3H
m, δ = 2.0–2.5; 4H

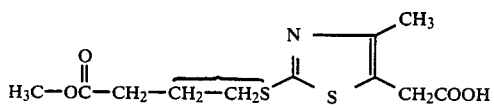

s, δ = 2.31; 3H
br. s; δ = 3.45; 1H
s, δ = 3.71; 2H
t, δ = 3.16; J = 7Hz; 2H

Stage 2

[2-(3-Carboxy-1-propylthio)-4-methyl-1,3-thiazol-5-yl]acetic acid 3.5 g of the compound obtained in stage 1 are dissolved in 20 ml of methanol, and the solution is stirred with 0.8 g of NaOH and 10 ml of water at room temperature for 6 h. The mixture is evaporated to dryness, the residue is again taken up with water, and the solution is acidified with 2N HCl solution. The precipitated product is filtered and recrystallized from ethyl acetate. 1.8 g of melting point 121° C. are obtained.

| Elemental analysis (C$_{10}$H$_{13}$NO$_4$S$_2$; 275.3) | | | | |
|---|---|---|---|---|
| calculated | C 43.6% | H 4.7% | N 5.1% | S 23.3% |
| found | 43.8% | 4.9% | 5.0% | 23.0% |

$^1$H-NMR (d$_6$-DMSO) δ=2.20 (s, 4—CH$_3$-thiazole, 3H), 1.70–2.60 (m, 2—CH$_2$CH$_2$S—thiazole, 4H), 3.15 (s, HOOCCH$_2$—, 2H), 3.73 (s, 5—CH$_2$COOH, 2H).

Examples 8-13 were synthesized as described in Example 7:

EXAMPLE 8:

2-(2-Carboxy-2-methoxyiminoethylthio)-4-methyl-1,3thiazol-5-ylacetic acid

Melting point: 138° C.

| Elemental analysis (C$_{10}$H$_{12}$N$_2$O$_5$S; 304.3) | | | | |
|---|---|---|---|---|
| calculated | C 39.5 | H 4.0% | N 9.2% | S 21.0% |
| found | 39.4% | 3.8% | 9.3% | 20.7% |

$^1$H-NMR (d$_6$-DMSO): δ=2.30 (s, 4—CH$_3$-thiazole, 3H), 3.63 (s, CH$_2$S, 2H), 3.93 (s, N-OCH$_3$, 3H), 4.06 (s, 5—CH$_2$-thiazole, 2H).

EXAMPLE 9

2-(2-Carboxy-2-hydroxyiminoethylthio)-4-methyl-1,3-thiazol-5-ylacetic acid

Melting point: 166°–7° C.

| Elemental analysis $_{10}$N$_2$O$_5$S; 290.3) | | | | |
|---|---|---|---|---|
| calculated | C 37.2% | H 3.5% | N 9.6% | S 22.1% |
| found | 37.5% | 3.6% | 9.9% | 22.4% |

$^1$H-NMR (d$_6$-DMSO): δ=2.23 (s, 4—CH$_3$-thiazole, 3H), 3.79 (s, CH$_2$, S, 2H), 4.03 (s, 5—CH$_2$-thiazole, 2H).

EXAMPLE 10

2-(4-Carboxybutylthio)-4-methyl-1,3-thiazol-5-ylacetic acid

Melting point: 110°–1° C.

| Elemental analysis (C$_{11}$H$_{15}$NO$_4$S$_2$; 289.3) | | | |
|---|---|---|---|
| calculated | C 45.7% | H 5.2% | N 4.8% |
| found | 45% | 5.4% | 4.7% |

$^1$H-NMR (d$_6$-DMSO):δ=1.6 and 2.2 and 3.1 (each m, —(CH$_2$)$_4$-8H), 2.23 (s, 4-thiazole-CH$_3$, 3H), 3.72 (s, 5-CH$_2$-thiazole, 2H).

EXAMPLE 11

2-(5-Carboxypentylthio)-4-methyl-1,3-thiazol-5-ylacetic acid

Melting point: 128°–9° C.

| Elemental analysis (C$_{12}$H$_{17}$NO$_4$S$_2$; 303.3) | | | |
|---|---|---|---|
| calculated | C 47.5% | H 5.6% | N 4.6% |
| found | 47.6% | 5.7% | 4.5% |

$^1$H-NMR (d$_6$-DMSO): δ=1.5 and 2.2 and 3.2 (each m, —(CH$_2$)$_5$—10H), 2.20 (s, 4—CH$_3$-thiazole, 3H), 3.76 (s, 5—CH$_2$-thiazole, 2H).

EXAMPLE 12

[2-(1-Carboxy-1-methylethylthio)-4-methyl-1,3-thiazol-5-yl]acetic acid

Melting point: 154°–5° C.
$^1$H-NMR (d$_6$-DMSO):δ=1.48 (s, (CH$_3$)$_2$C, 6H) 2.25 (s, 4-CH$_3$-thiazole, 3H), 3.80 (s, 5-CH$_2$COOH-thiazole, 2H).

EXAMPLE 13

[2-(1-Carboxy-1-cyclobutylthio)-4-methyl-1,3-thiazol-5-yl]acetic acid

Melting point: 114°–5° C.
$^1$H-NMR (d$_6$-DMSO):δ=1.8–2.6 (m, 6H, cyclobutyl-H), 2.20 (s, 4-CH$_3$-thiazole, 3H), 3.75 (S, 5-CH$_2$CO).

EXAMPLE 14

4-Carboxy-5-ethylthio-1,3-thiazole 6 g of methyl 5-ethylthio-1,3-thiazole-4-carboxylate were dissolved in 100 ml of methanol and heated with 1.2 g of NaOH in 10 ml of water under reflux for about 1 h. After the solvent had been removed in a rotary evaporator, the solids were removed by filtration, and the filtrate was acidified with 2N HCl solution. After drying, 4.7 g of the title compound, of melting point 158°–9° C., were obtained.

$^1$H-NMR (d$_6$-DMSO):δ (ppm): 1.2 (t, ethylthio-CH$_3$, J=7 Hz, 3H), 2.9 (q, ethylthio-CH$_2$, J=7 Hz, 2H), 8.8 (s, thiazole-2H, 1H).

MS: molecular peak 189 (C$_6$H$_7$NO$_2$S$_2$).

EXAMPLE 15

5-Carboxymethylthio-1,3-thiazol-4-ylcarboxylic acid 12.3 g of methyl 5-methoxycarbonylmethylthio-1,3-thiazol-4-ylcarboxylate were dissolved in 100 ml of methanol and heated with 2 g of NaOH in 20 ml of water under reflux for 2 h. After the methanol had been removed in a rotary evaporator, the mixture was clarified by filtration and the filtrate was acidified with 2N HCl solution. After drying, 10.3 g of melting point 237° C. were obtained.

$^1$H-NMR (d$_6$-DMSO): δ (ppm): 3.9 (s, HOOCCH$_2$S, 2H), 8.8 (s, thiazole-2H, 1H).

IR (KBr disk): ν=1680 cm$^{-1}$ (thiazole-COOH), 1710 Cm$^{-1}$ (—SCH$_2$COOH).

EXAMPLE 16

Disodium salt of 5-carboxymethylthio-1,3-thiazol-4-yl-carboxylic acid 24 g of the dicarboxylic acid from Example 32 and 8.8 g of NaOH are dissolved in about 50 ml of warm water. Methanol is added until slightly opalescent, and crystallization is allowed to go to completion while cooling. Filtration provided 23.5 g of disodium salt of melting point >300° C.

| Elemental analysis (C$_6$H$_3$NO$_4$S$_2$Na$_2$ × H$_2$O; 281.4) | | |
|---|---|---|
| calculated | H$_2$O 6.4% | Na 16.3% |
| found | 7.4% | 16.0% |

EXAMPLE 17

[4-(4-Carboxy-1,3-thiazol-5-yl)thio]butyric acid 4 g of the dimethyl ester of the title compound were dissolved in about 20 ml of ethanol and heated under reflux with 1.5 g of NaOH in 5 ml of water for 1 h. After removal of the solvent in a rotary evaporator, and filtration of the aqueous solution, it was acidified with 2N HCl solution. After the precipitate had been filtered off and dried, 2.7 g of title compound of melting point 177° C. were obtained.

$^1$H-NMR (d$_6$-DMSO): δ (ppm): 1.9 (m, S-CH$_2$CH$_2$CH$_2$COOH, 2H), 2.4 and 3.1 (each t, S—CH$_2$—CH$_2$CH$_2$COOH, each 2H, J=7 Hz), 8.9 (s, thiazole-2H).

IR (KBr disk): ν=1680 cm$^{-1}$ (thiazole-4-COOH), 1707 cm$^{-1}$ (s-(CH$_2$)$_3$COOH).

EXAMPLE 18

[3-(4-Carboxy-1,3-thiazol-5-yl)thio]propionic acid 13 g of the dimethyl ester of the title compound were dissolved in 200 ml of methanol and heated under reflux on a steam bath with 4 g of NaOH in 25 ml of water. After removal of the methanol by distillation, and filtration of the aqueous phase, it was acidified with 2N HCl solution to precipitate the acid. After drying, 2.3 g of melting point 172° C. were obtained.

IR (KBr disk): ν=3090 cm$^{-1}$ (C—H-thiazole), 1700 cm$^{-1}$ (COOH).

$^1$H-NMR (d$_6$-DMSO): δ (ppm): 2.7 and 3.2 (each t, —S—CH$_2$CH$_2$COOH, J≈7 Hz, each 2H), 8.9 (s, thiazole-2-H, 1H).

EXAMPLE 19

[5-(4-Carboxy-1,3-thiazol-5-yl)thio]pentanoic acid disodium salt 20 g of the dimethyl ester of the title compound were dissolved in 100 ml of methanol and 100 ml of water, and 5.6 g of NaOH were added. The mixture was heated under reflux for about 1 h, the methanol was removed by distillation, and the aqueous phase was filtered and acidified with 2N HCl solution. After drying, 15 g of melting point 187°–190° C. were obtained. This amount was dissolved in a little water containing 4.2 g of NaOH, and acetone was added. The resulting precipitate was filtered off and dried. 17.5 g of title compound of melting point 210° C. (decomposition) were obtained.

$^1$H-NMR (D$_2$O):δ (ppm): 1.7 and 2.2 and 3.0 (each m, —SCH$_2$CH$_2$CH$_2$CH$_2$CO$_2$, 4 and 2 and 2H), 8.6 (s, thiazole-2H, 1H).

| Elemental analysis (C$_9$H$_9$NO$_4$S$_2$Na$_2$ × 1.5 H$_2$O; 332.3) | | | | | |
|---|---|---|---|---|---|
| calculated | C 32.4% | H 3.6% | N 4.2% | Na 13.8% | H$_2$O 8.1% |
| found | 32.5% | 3.7% | 4.1% | 14.0% | 8.8% |

EXAMPLE 20

[6-(4-Carboxy-1,3-thiazol-5-yl)thio]hexanoic acid disodium salt 20 g of the dimethyl ester of the title compound were dissolved in 200 ml of water/methanol (1:1), and this methanol was heated with 5.4 g of NaOH under reflux on a steam bath for 1 h. After removal of the methanol by distillation, the aqueous phase was clarified, acidified with 2N HCl solution, and the dicarboxylic acid was filtered off. Yield 16.6 g of melting point 151°–2° C. The amount thus obtained was dissolved in 4.4 g of NaOH in a little water, and the disodium salt was precipitated with acetone.

Yield: 18.5 g of melting point 164°–6° C. (decomposition).

$^1$H-NMR (D$_2$O): δ (ppm): 1.6 and 2.2 and 3.0 (each m, —S—(CH$_2$)$_5$—CO$_2$, 6 and 2 and 2H), 8.6 (s, thiazole-2H, 1H).

| Elemental analysis (C$_{10}$H$_{11}$NO$_4$S$_2$Na$_2$ × 1H$_2$O; 337.3) | | | | | |
|---|---|---|---|---|---|
| calculated | C 35.6% | H 3.9% | N 4.1% | Na 13.6% | H$_2$O 5.4% |
| found | 34.8% | 4.0% | 4.0% | 13.3% | 6.9% |

EXAMPLE 21

(2-Carboxymethylthio-1,3-thiazol-5-yl)acetic acid 2.97 g of (2-mercapto-1,3-thiazol-5-yl)acetic acid were dissolved in 17 ml of 2N NaOH solution. To this were added 2.78 g of bromoacetic acid, and the mixture was heated under reflux on a steam bath for 3 h. After the mixture had cooled, it was clarified and acidified with 2N HCl solution. Allowing crystallization to go to completion overnight in a refrigerator provided 1.4 g of melting point 120°–1° C.

$^1$H-NMR (d$_6$-DMSO) δ (ppm): 3.65 (s, S—CH$_2$COOH, 2H); 3.8 (s, thiazole—CH$_2$COOH, 2H); 7.3 (s, thiazole-4H, 1H).

MS: M$^+$=233 (C$_7$H$_7$NO$_4$S$_2$).

EXAMPLE 22

[2-(3-Carboxypropylthio)-1,3-thiazol-5-yl]acetic acid 1.5 g of [2-(3-methoxycarbonylpropylthio)-1,3-thiazol-5-yl]acetic acid in 5 ml of methanol and 7 ml of aqueous 2N NaOH solution were heated under reflux on a steam bath for 3 h. After removal of the methanol in a rotary evaporator and clarification of the aqueous solution, it was acidified with 2N HCl solution and, after crystallization was complete, 0.6 g of melting point 97° C. was obtained.

$^1$H-NMR (d$_6$-DMSO): δ (ppm): 2.0 (m, SCH$_2$CH$_2$CH$_2$COOH, 2H), 2.4 and 3.2 (each t, S—CH$_2$CH$_2$CH$_2$COOH, each 2H, J=7 Hz), 3.8 (s, thiazole CH$_2$COOH, 2H), 7.3 (s, thiazole-4H, 1H).

LR (KBr disk): ν=3100 cm$^{-1}$ (thiazole-4H stretching), 1680 cm$^{-1}$ and 1710 cm$^{-1}$ (COOH).

EXAMPLE 23

[2-(2-Carboxybenzyl)thio-4-methyl-1,3-thiazol-5-yl]acetic acid

Stage 1

Methyl [2-(2-methoxycarbonylbenzyl)thio-4-methyl-1,3-thiazol-5-yl]acetate 4.1 g of methyl 2-mercapto-4-methyl-1,3-thiazol-5-yl-acetate were dissolved in 50 ml of DMF and, in the presence of 5 g of ground potassium carbonate, 5.1 g of methyl 2-bromomethylbenzoate were added dropwise. After the evolution of heat had subsided, the mixture was stirred for 1 h, filtered, and DMF was removed in a rotary evaporator. The residue was taken up in ethyl acetate and washed 2× with water. The organic phase was dried, and the solvent was removed in vacuo. 5.6 g of an oil were obtained.

$^1$H-NMR (CDCL$_3$): δ (ppm): 2.3 (s, thiazole-4-CH$_3$, 3H), 3.60 (s, thiazole-5-CH$_2$, 2H), 3.65 (s, thiazole—5—CH$_2$COOCH$_3$, 3H), 3.8 (s, aromat. COOCH$_3$, 3H), 4.7 (s, aromat. CH$_2$, 2H), 7.1 (m, aromat. H, 4H).

Stage 2

Title Compound 3.8 g of stage 1 are dissolved in 35 ml of methanol, and the solution is heated with 0.9 g of NaOH in 5 ml of water under reflux on a steam bath for 2 h. Methanol is removed in a rotary evaporator, and the aqueous solution is clarified and acidified with 2N HCl solution. The precipitated product is recrystallized from isopropanol. Yield 1.5 g of melting point 199° C.

$^1$H-NMR (d$_6$-DMSO): δ (ppm): 2.2 (s, thiazole-4-CH$_3$, 3H), 3.6 (s, thiazole-5-CH$_2$, 2H), 4.6 (s, CH$_2$S, 2H), 7.2–7.8 (m, aromat. H, 4H).

IR (KBr disk): ν=1680 cm$^{-1}$ and 1710 cm$^{-1}$ (COOH).

EXAMPLE 24

1-Phenyl-3-hydroxy-1,2,4-triazol-5-ylmercaptoacetic acid 0.96 g (5 mmol) of 1-phenyl-3-hydroxy-5-mercapto-1,2,4-triazole are dissolved in 15 ml of DMF.

0.7 g (5 mmol) of potassium carbonate, finely powdered, and 0.6 g (6 mmol) of chloroacetic acid are added.

After the mixture has foamed briefly it is stirred at room temperature for 4 hours. The NaCl is filtered off with suction, and DMF is removed by distillation under high vacuum at room temperature.

The residue is washed with water and dried.

Yield: 0.52 g=41%, melting point 202° C. (decomposition).

IR (KBr) ν=3440; 1730; 1630 cm$^{-1}$.

$^1$H-NMR (d$_6$-DMSO): δ=12.33 ppm s(1H); 7.50 ppm s(5H) arom; 4.03 ppm s(2H) S—CH$_2$—.

1-Methyl-3-hydroxy-1,2,4-triazol-5-ylmercaptoacetic acid 1.3 g (10 mmol) of 1-methyl-3-hydroxy-5-mercapto-1,2,4-triazole are dissolved in 20 ml of DMF, and 1.1 g (11.6 mmol) of chloroacetic acid are introduced.

The mixture is stirred at 50° C. for 16 h, then evaporated in a rotary evaporator, and the residue is extracted by stirring with ether several times. The white precipitate is washed with ether.

Melting point 240° C., yield 1.4 g=75%

IR (KBr) ν=3000–2500 cm$^{-1}$ OH stretching vibration; 1725 cm$^{-1}$ saturated carboxylic acid.

NMR (TFA) δ=4.15 ppm (s, 2H); 4.03 ppm (s, 3H).

EXAMPLE 25

2,5-Dicarboxymethylthio-1,3,4-thiadiazole 2.55 g of bromoacetic acid were added to 3.54 g of 2,5-dimercapto-1,3,4-thiadiazole dissolved in 17 ml of 1N NaOH.

The mixture was heated on a steam bath for 3 hours, filtered, cooled to +5° C., and the pH was adjusted to 1.8 with 2N HCl. The precipitate was filtered off with suction, washed with H$_2$O and dried in vacuo.

Yield: 3.44 g, melting point: 168° C.

NMR (DMSO-d$_6$) 4.15 ppm, s, 4H, CH$_2$.

EXAMPLE 26

2,5-Dicarboxyethylthio-1,3,4-thiadiazole 1.22 g of 3-bromopropionic acid were added to 904 mg of disodium 1,3,4-thiadiazole-2,5-dithiolate dissolved in 30 ml of DMF.

The mixture was stirred at room temperature for 18 h, filtered, and the mother liquor was evaporated, and the residue was taken up in H$_2$O. The pH was adjusted to 1.8 with 2N HCl. The precipitate was filtered off with suction, washed with H$_2$O and dried in vacuo.

Yield: 0.7 g, melting point: 140° C.

NMR (DMSO-d$_6$): 2.7 ppm, t, 4H, CH$_2$CO$_2$; 3.4 ppm, t, 4H, CH$_2$S.

EXAMPLE 27

2,5-Di(3-carboxy-1-propylthio)-1,3,4-thiadiazole

If 1.56 g of 4-bromobutyric acid is reacted in analogy to Example 26, then 990 mg of the title compound are obtained.

Melting point: 111° C.

NMR (DMSO-d$_6$): 1.7 - 2.6 ppm, m, 8H, CH$_2$CH$_2$CO$_2$; 3.3 ppm, t, 4H, CH$_2$-S.

The examples which follow were carried out in analogy to Example 23.

EXAMPLE 28

2-(3-Carboxybenzyl)thio-4-methyl-1,3-thiazol-5-yl]acetic acid

Stage 1

Methyl [2-(3-methoxycarbonylbenzyl)thio-4-methyl-1,3-thiazol-5-yl]acetate

From
4.1 g of methyl 2-mercapto-4-methyl-1,3-thiazol-5-yl-acetate and
5.1 g of methyl 3-bromomethylbenzoate were obtained 5.0 g of oil.

$^1$H-NMR (CDCL$_3$): δ (ppm): 2.3 (s, thiazole-4-CH$_3$, 3H), 3.60 and 3.62 (2×s, thiazole-5—CH$_2$, 2H; thiazole-5-CH$_2$ COOCH$_3$, 3H), 3.8 (s, aromat. COOCH$_3$, 3H), 4.4 (s, aromat. CH$_2$, 2H), 6.8–7.8 (m, aromat. H, 4H).

Stage 2

Title Compound

From
2.4 g of stage 1, 1.2 g of title compound of melting point 221° C. were obtained.

$^1$H-NMR (d$_6$-DMSO): δ (ppm): 2.25 (s, thiazole-4-CH$_3$, 3H), 3.72 (s, thiazole-5CH$_2$, 2H), 4.5 (s, aromat. CH$_2$, 2H), 7.3–8.0 (m, aromat. H, 4H).

IR (KBr disk): ν=1710 cm$^{-1}$ (COOH), 2500 cm$^{-1}$ (OH).

EXAMPLE 29

[2-(4-Carboxybenzyl)thio-4-methyl-1,3-thiazol-5-yl]-acetic acid

Stage 1

Methyl [2-(4-methoxycarbonylbenzyl)thio-4-methyl-1,3-thiazol-5-yl]acetate

From
6.1 g of methyl 2-mercapto-4-methyl-1,3-thiazol-5-yl-acetate and
8.6 g of methyl 4-bromomethylbenzoate were obtained 6.7 g of oil.

$^1$H-NMR (CDCl$_3$)=δ(ppm): 2.3 (S, thiazole-4-CH$_3$, 3H), 3.55 (s, thiazole-5-CH$_2$, 2H), 3.6 (s, thiazole-5-CH$_2$COOCH$_3$, 3H), 3.78 (s, aromat. COOCH$_3$, 3H), 4.3 (s, aromat. CH$_2$, 2H), 7.25 and 7.80 (each d, J=8 Hz, aromat. H, 4H).

IR (film): ν=1710 cm$^{-1}$ and 1725 cm$^{-1}$ (COOCH$_3$).

Stage 2

Title Compound

From 6.7 g of stage 1 were obtained 4.2 g of the title compound of melting point 196° C. (i-propanol). $^1$H-NMR (d$_6$-DMSO): δ(ppm)=2.17 (s, 4-thiazole-CH$_3$), 3H), 3.70 (s, 5-thiazole CH$_2$, 2H), 4.48 (S, aromat. CH$_2$, 2H), 7.35 and 7.85 (each d, J=8 Hz, aromat. H, 4H).

IR (KBr disk): ν=1700 cm$^{-1}$ (COOH), 2500 cm$^{-1}$ (OH).

| Elemental analysis: C$_{14}$H$_{13}$NO$_4$S (323.3) | | | |
|---|---|---|---|
| calculated | C 52.0% | H 4.1% | N 4.3% |
| found | 52.1% | 4.2% | 4.0% |

Examples 30 to 33 were synthesized as described in Example 5.

EXAMPLE 30

2-Carboxymethylthio-5-hydroxy-1-methyl-6-oxodihydro-1,3,4-triazine

NMR (DMSO-d$_6$) δ=3.98 ppm (s, CH$_2$); δ=3.32 ppm (s, CH$_3$).

EXAMPLE 31

2-Carboxyethylthio-5-hydroxy-1-methyl-6-oxodihydro-1,3,4-triazine

NMR (DMSO-d$_6$)δ=3.28 ppm (s, CH$_3$); δ=3.18 ppm (t, CH$_2$); δ=2.73 ppm (t, CH$_2$).

EXAMPLE 32

4-Carboxyethyl-2-carboxymethylthio-1,3-thiazole

NMR (DMSO - d$_6$)δ=7.28 ppm (s, thiazole-H); δ=4.1 ppm (s, CH$_2$); δ=3.3 ppm (m, 2×CH$_2$).

EXAMPLE 33

4-Carboxyethyl-2-carboxyethylthio-1,3-thiazole

NMR (DMSO - d$_6$)δ=7.18 ppm (s, thiazole-H); δ=3.5 ppm (t, CH$_2$); δ=3.3 ppm (m, 2×CH$_2$); δ=2.7 ppm (t, CH$_2$).

EXAMPLE 34

4-Carboxy-2-carboxyethylthio-1,3-thiazole 6.9 g of bromopropionic acid were dissolved in 100 ml of water, and the pH was adjusted to 7 with 1N NaOH. This solution was added dropwise to a suspension of 7.5 g of 4-ethoxycarbonyl-2-mercapto-1,3-thiazole in 75 ml of H$_2$O. The pH was adjusted to 8-10 with 2N NaOH, and the mixture was stirred at room temperature for 4 h and at 60° C. for 2 h. The pH was maintained between 8 and 10. While cooling in ice, the mixture was acidified to pH 1 with 2N HCl, and the product was filtered off.

Yield: 7.6 g of the title compound.

NMR (DMSO-d$_6$)δ=8.35 ppm (s, thiazole-H); δ=3.52 ppm (t, CH$_2$); δ=2.75 ppm (t, CH$_2$).

EXAMPLE 35

5-Carboxy-2-carboxymethylthio-4-methyl-1,3-thiazole

Stage 1

6 g of bromoacetic acid were dissolved in 50 ml of water, and the pH was adjusted to 7-8 with 1N NaOH. The solution was heated to 60° C., 8 g of 5-ethoxycarbonyl-2-mercapto-4-methyl-1,3-thiazole were added, and the mixture was stirred at this temperature and at pH 8-10 for 2 h. While cooling in ice, the mixture was acidified to pH 1 with 2N HCl, and the product was filtered off with suction. 10.9 g.

Stage 2

2.61 g of the product obtained in stage 1 were dissolved in 20 ml of ethanol, and 1.96 g of KOH in 70 ml of ethanol were added. The mixture was stirred at 50°–60° C. for ½ h, diluted with 60 ml of H$_2$O and, while cooling in ice, acidified to pH 0.5 with half-concentrated HCl. Ethanol was removed in a rotary evaporator, whereupon the product precipitated out. It was filtered and washed with H$_2$O; yield: 2.05 g of the title compound.

NMR (DMSO-d$_6$)δ=4.08 ppm (s, CH$_2$); δ=2.52 ppm (s, CH$_3$).

Examples 36–37 were prepared as described in Example 35.

EXAMPLE 36

4-Carboxy-2-carboxymethylthio-1,3-thiazole

NMR (DMSO-d$_6$)δ=8.23 ppm (s, thiazole-H); δ=4.12 ppm (s, CH$_2$).

EXAMPLE 37

5-Carboxy-2-carboxyethylthio-4-methyl-1,3-thiazole

NMR (DMSO-d$_6$)δ=3.5 ppm (t, CH$_2$); δ=2.75 ppm (t, CH$_2$); δ=2.57 ppm (s, CH$_3$).

EXAMPLE 38

4-Carboxy-2-carboxypropylthio-1,3-thiazole

Stage 1

8.3 g of 4-ethoxycarbonyl-2-mercapto-1,3-thiazole in 100 ml of acetone were stirred together with 6.1 g of K$_2$CO$_3$ and 10.3 g of ethyl bromobutyrate at room temperature for ¾ h. The mixture was filtered, and the filtrate was evaporated to dryness. The residue was taken up in ethyl acetate and extracted 2× with H$_2$O. After evaporation of the solvent, 14 g of an oil remained.

Stage 2

13.8 g of the product from stage 1 were dissolved in 80 ml of ethanol, and 11.6 g of KOH in 250 ml of ethanol were added. The mixture was stirred at room temperature for 3 h, and the precipitated potassium salt was filtered off. The salt was dissolved in 150 ml of water and, at 0° C., the pH was adjusted to 0.5 with ½-concentrated HCl, whereupon the product precipitated out: 8.7 g of the title compound.

NMR (DMSO-d$_6$)δ=8.22 (s, thiazole-H); δ=3.25 (t, CH$_2$); δ=2.38 (t, CH$_2$); δ=1.92 (q, CH$_2$).

Examples 39–41 were prepared as described in Example 38.

EXAMPLE 39

5-Carboxy-2-carboxypropylthio-4-methyl-1,3-thiazole

NMR (DMSO-d$_6$)δ=3.27 ppm (t, CH$_2$); δ=2.58 ppm (s, CH$_3$); δ=2.38 ppm (t, CH$_2$); δ=1.93 ppm (q, CH$_2$).

EXAMPLE 40

2-Carboxypropylthio-5-hydroxy-1-methyl-6-oxodihydro-1,3,4-triazine

NMR (DMSO-d$_6$)δ=3.28 ppm (s, CH$_3$); δ=3.07 ppm (t, CH$_2$); δ=2.37 ppm (t, CH$_2$); δ=1.93 ppm (q, CH$_2$).

EXAMPLE 41

5-Carboxy-2-carboxybutylthio-4-methyl-1,3-thiazole

NMR (DMSO-d$_6$) δ=3.23 ppm (t, CH$_2$); δ=2.57 ppm (s, CH$_3$); δ=2.27 ppm (t, CH$_2$); δ=1.73 ppm (m, 2×CH$_2$).

EXAMPLE 42

5-Acetamido-2-carboxymethylthio-1,3-thiazole 3.48 g (20 mmol) of 5-acetamido-2-mercapto-1,3-thiazole were dissolved in 90 ml of dry DMF, 2.78 g (20 mmol) of bromoacetic acid were added, and the mixture was stirred at room temperature for 2 hours. The solvent was then removed in vacuo, and the solid residue was washed with diethyl ether. After recrystallization from isopropanol/diethyl ether, 3.1 g (67%) of the title compound were obtained.

$^1$H - NMR (d$_6$-DMSO): δ=2.10 ppm (s, 3H, —CH$_3$), 3.93 ppm (s, 2H, —CH$_2$—), 7.40 ppm (s, 1H, thiazole-H), 7.90 ppm (br s, —CO$_2$H and H$_2$O), 11.43 ppm (br, s, 1H, —NH).

The substances described in Examples 43 to 48 were synthesized in analogy to Example 42.

EXAMPLE 43

Monoamide of N-(2-carboxymethylthio-1,3-thiazol-5-yl)-glutaric acid $^1$H - NMR (d$_6$-DMSO): δ=1.56–2.65 ppm (m, 6H, —CH$_2$—CH$_2$—CH$_2$—), 3.90 ppm (s, 2H, —CH$_2$S), 7.36 ppm (s, 1H, thiazole-H), 8.26 ppm (br s, —CO$_2$H and H$_2$O), 11.40 ppm (br s, 1H, —NH—).

EXAMPLE 44

Monoamide of N-(carboxymethylthio-1,3-thiazol-5-yl)-succinic acid $^1$H - NMR (d$_6$-DMSO): δ=2.40–2.45 ppm (m, 4H, —CH$_2$—CH$_2$—), 3.90 ppm (s, 2H, —CH$_2$S—), 7.33 ppm (s, 1H, thiazole-H), 9.26 ppm (br s, —CO$_2$H and H$_2$O), 11.46 ppm (br s, 1H, —NH—).

EXAMPLE 45

(R,S)-2-(Carboxymethylthio)-6-carboxy-4,5,6,7-tetrahydro-1,3-benzothiazole $^1$H - NMR (d$_6$-DMSO): δ=1.75–1.91 and 2.05–2.15 ppm (two m, 2H, —CH$_2$—on thiazole-C-5), 2.51 ppm (br s, 1H, —CH—CO$_2$—), 2.61–3.01 ppm (m, 4H, —CH$_2$—CH$_2$—) 4.03 ppm (s, 2H, —CH$_2$S—).

EXAMPLE 46

2-(Carboxymethylthio)benzothiazole

Melting point 144°–6° C. IR 1710 cm$^{-1}$.
$^1$H - NMR (d$_6$-DMSO): δ=4.23 ppm (s, 2H, —CH$_2$), 7.2–8.0 ppm (m, 4H, aryl-H).

EXAMPLE 47 2-(Carboxymethylthio)benzimidazole

Melting point 172°–4° C. IR 1640, 1720 cm$^{-1}$.
$^1$H - NMR (d$_6$-DMSO): δ=4.27 ppm (s, 2H, —CH$_2$), 7.2–7.4 ppm (m, 4H, aryl-H).

EXAMPLE 48

2-(Carboxymethylthio)-5-carboxybenzimidazole

Melting point 228°–230° C. IR 1610, 1700 cm$^{-1}$.
$^1$H - NMR (d$_6$-DMSO): δ=3.97 ppm (s, 2H, —CH$_2$), 7.4–8.03 (m, 3H, aryl-H).

EXAMPLE 49

3-[2-(Carboxymethylthio)-4-methyl-1,3-thiazol-5-yl]propionic acid 2 g (8.6 mmol) of ethyl 3-(2-mercapto-4-methyl-1,3-thiazol-5-yl)propionate were initially introduced into 40 ml of dry DMF, and 1.49 g (8.6 mmol) of bromoacetic acid were added. After 2 hours, the solvent was removed in vacuo, and 3.8 g of ethyl 3-[2-(carboxymethylthio)-4-methyl-1,3-thiazol-5-yl]propionate were obtained as an oil. The crude product was taken up in 25 ml of ethanol, 33 ml of 1N sodium hydroxide solution were added, and the reaction mixture was heated at 50° C. After the reaction was complete, the ethanol was removed in vacuo, and the aqueous residue was taken up in concentrated hydrochloric acid at pH 3.0, and the solution was extracted with ethyl acetate. 1.6 g (71%) of the title compound were obtained from the organic phase after drying with MgSO$_4$, evaporation and crystallization with diethyl ether.

$^1$H - NMR (d$_6$-DMSO): δ=2.23 ppm (s, 3H, —CH$_3$), 2.25–3.15 ppm (m, 4H, —CH$_2$—CH$_2$—), 3.96 ppm (s, 2H, —CH$_2$S—).

EXAMPLE 50

(R,S)-2-(2-Carboxyethylthio)-6-carboxy-4,5,6,7-tetrahydro-1,3-benzothiazole 1.15 g (5 mmol) of (R,S)-6-methoxycarbonyl-4,5,6,7-tetrahydro-2-mercaptobenzothiazole were dissolved in 50 ml of acetone, 888 mg (6.5 mmol) of powdered K$_2$CO$_3$ and 0.77 ml (5 mmol) of ethyl 3-bromopropionate were added, and the reaction mixture was stirred at room temperature for 3 hours. Then a solid residue was filtered off, and the filtrate was evaporated. The crude product (1.6 g) was hydrolysed with 2N sodium hydroxide solution and ethanol. The ethanol was then distilled off, and the aqueous residue was adjusted to pH 3 with 2N hydrochloric acid, whereupon 480 mg (33%) of the title compound were obtained as a solid.

$^1$H - NMR (d$_6$-DMSO): δ=1.4–3.0 ppm (m, 11H, 5 CH$_2$ groups and 1 CH).

EXAMPLE 51

3-[2-(3-Carboxy-1-propylthio)-4-methyl-1,3-thiazol-5-yl]-propionic acid 2 g (8.6 mmol) of ethyl 3-[2-mercapto-4-methyl-1,3-thiazol-5-yl]propionate were initially introduced into 40 ml of dry DMF, and 1.48 g (11 mmol) of powdered K$_2$CO$_3$ and 1.23 ml (8.6 mmol) of ethyl 4-bromobutyrate were added, and the reaction mixture was stirred at 50° C. for 2 hours. A solid residue was filtered off with suction, the DMF was removed in vacuo, and 3.6 g of a crude product were obtained, and this was taken up in 25 ml of ethanol. After addition of 1N sodium hydroxide solution, the mixture was stirred at room temperature for 2 hours, and the ethanol was removed in vacuo, and the aqueous residue was adjusted to pH 3 with hydrochloric acid. The solution was extracted with ethyl acetate, and the organic phase was dried with MgSO$_4$ and evaporated. 2.2 g (88%) of the title compound were obtained as an oil.

$^1$H - NMR (CDCl$_3$): δ=1.66–2.5 and 2.6–3.15 ppm (2 m, 10H, 5 CH$_2$ groups), 2.16 ppm (s, 3H, —CH$_3$), 6.4 ppm (br s, 2H, —CO$_2$H).

Examples 52 to 56 were prepared as described in Example 51.

EXAMPLE 52

2-(Carboxy-1-propylthio)-6-carboxy-4,5,6,7-tetrahydro-1,3-benzothiazole $^1$H - NMR (d$_6$-DMSO): δ=1.5–3.2 ppm (m, 13H, 6 CH$_2$ groups and 1 CH).

EXAMPLE 53

2-(Carboxy-1-propylthio)-5-carboxybenzimidazole

Melting point 198°–200° C. IR 1700 cm$^{-1}$.

$^1$H - NMR (d$_6$-DMSO): δ=1.83–2.40 ppm (m, 4H, —CH$_2$—CH$_2$), 3.37 ppm (t, 2H, —CH$_2$S), 7.4–8.0 ppm (m, 3H, aryl-H).

EXAMPLE 54

2-(Carboxy-1-propylthio)benzimidazole

Melting point 158°–9° C. IR 1710 cm$^{-1}$.

$^1$H - NMR (d$_6$-DMSO): δ=1.83–2.56 ppm (m, 4H, —CH$_2$—CH$_2$), 3.57 ppm (t, 2H, —CH$_2$S), 7.3–7.8 ppm (m, 4H, aryl-H).

EXAMPLE 55

3-Hydroxy-5-(3-carboxy-1-propylthio)-1-phenyl-1,2,4-triazole

Melting point 182° C. IR 1730 cm$^{-1}$.

$^1$H - NMR (d$_6$-DMSO): δ=1.76–2.23 ppm (m, 4H, —CH$_2$—CH$_2$), 3.13 ppm (t, 2H, —CH$_2$S), 7.33 ppm (m, 5H, aryl-H), 8.85 ppm (br s, 1H, OH).

EXAMPLE 56

2-(Carboxy-1-propylthio)benzothiazole

Melting point 100° C. IR 1710 cm$^{-1}$.

$^1$H - NMR (d$_6$-DMSO): δ=2.03–2.08 ppm (m, 4H, —CH$_2$—CH$_2$), 3.45 ppm (t, 2H, —CH$_2$S), 7.18–7.9 ppm (m, 4H, aryl-H).

EXAMPLE 57

2-(4-Carboxybenzylthio)benzimidazole 4.6 g (30 mmol) of 2-mercaptobenzimidazole were initially introduced into 60 ml of dry DMF, 8.3 g (60 mmol) of K$_2$CO$_3$ were added, and a solution of 6.7 g (31 mmol) of α-bromo-4-toluic acid in 15 ml of dry DMF was added dropwise at room temperature. After 4 hours, a solid residue was filtered off with suction, the DMF was removed in vacuo, and the residue was taken up in aqueous hydrochloric acid at pH 2. Crystals of the title compound separated out, and these were washed with water, methanol and ether and dried.

Yield: 7.1 g (84%).

Melting point 263°–5° C. IR 1710 cm$^{-1}$.

$^1$H - NMR (d$_6$-DMSO): δ=4.90 ppm (s, 2H, —CH$_2$), 7.27–7.93 ppm (m, 4H, aryl-H).

Examples 58 to 60 were prepared as described in Example 57.

EXAMPLES 58

3-Hydroxy-5-(4-carboxybenzylthio)-1-methyl-1,2,4-triazole

Melting point 298° C. IR 1710 cm$^{-1}$.

$^1$H - NMR (d$_6$-DMSO): δ=3.43 ppm (s, 3H, —CH$_3$), 4.37 ppm (s, 2H, benzyl-H), 7.33–7.93 ppm (m, 4H, aryl-H).

EXAMPLE 59

2-(4-Carboxybenzylthio)benzothiazole

Melting point 190°–192° C. IR 1680–1710 cm$^{-1}$.
$^1$H - NMR (d$_6$-DMSO): δ=4.70 ppm (s, 2H, —CH$_2$), 7.23–7.86 ppm (m, 4H, aryl-H).

EXAMPLE 60

3-Hydroxy-5-(4-carboxybenzylthio)-1-phenyl-1,2,4-triazole

Melting point 138°–140° C. IR 1700 cm$^{-1}$.
$^1$H - NMR (d$_6$-DMSO): δ=4.45 ppm (s, 2H, —CH$_2$S), 7.4–7.93 ppm (m, 5H, aryl-H):

EXAMPLE 61

4-(3-Carboxy-1-methyl-1,2,4-triazol-5-yl)thiobutyric acid

Stage 1

Methyl 4-(3-methoxycarbonyl-1-methyl-1,2,4-triazol-5-yl)-thiobutyrate 1.9 g of ethyl 1-methyl-5-mercapto-1,2,4-triazol-3-yl-carboxylate are dissolved in 30 ml of acetone, 1.8 g of methyl 4-chlorobutyrate are added, and the mixture is heated under reflux in the presence of 2.8 g of ground K$_2$CO$_3$ (potash) for 2 h. After filtration and removal of the solvent, the residue is chromatographed on silica gel using ethyl acetate (Rf: about 0.6), and the product fraction is evaporated.
Yield: 1.5 g of oily product.

$^1$H—NMR (CDCl$_3$):

δ (ppm) = 1.3 (t, OCH$_2$CH$_3$, 3H)
= 2.2, 2.4 and 3.4
(each m, S—CH$_2$CH$_2$CH$_2$—COO, 6H)
= 3.5 amd 3.8
(each s, N—CH$_3$ and COOCH$_3$, 6H)
= 4.3 (q, O—CH$_2$CH$_3$, 2H)

Stage 2

Title Compound 1.5 g of stage 1 are dissolved in 5 ml of methanol, 2.8 ml of 2 N NaOH are added, and the mixture is heated on a steam bath for 1 h. The solution is clarified with active charcoal, cooled, and the pH is adjusted to about 4 with 2 N HCl. Filtration and drying of the product provide 0.8 g of melting point 118°–120° C.

$^1$H—NMR (d$_6$-DMSO):

δ (ppm) = 1.9(q, —CH$_2$CH$_2$CH$_2$—, 2H)
= 2.4 and 3.2 (each t, —CH$_2$CH$_2$CH$_2$—, 4H)
= 3.8 (s, N—CH$_3$, 3H)

The following Examples 62-63 were carried out in analogy to Example 61.

EXAMPLE 62

2-(3-Carboxypropylthio)nicotinic acid 3.3 g of title compound, of melting point 188° C., were obtained from 3.4 g of methyl 2-mercaptonicotinate and 3.6 g of methyl 4-chlorobutyrate after alkaline hydrolysis.

| Elemental analysis: (C$_{10}$H$_{11}$NO$_4$S; 241.3) | | | | |
|---|---|---|---|---|
| calculated | C 49.8% | H 4.6% | N 5.8% | S 13.3% |
| found | 49.6% | 4.5% | 5.8% | 13.4% |

$^1$H—NMR (d$_6$-DMSO):

δ (ppm) = 1.9 (q, —CH$_2$CH$_2$CH$_2$—, 2H)
= 2.3 and 3.2 (each t, —CH$_2$CH$_2$CH$_2$—, 4H)
7.1, 8.1 and 8.5 (m, pyridine-H, 3H)

EXAMPLE 63

6-(3-Carboxypropylthio)nicotinic acid 0.76 g of methyl 6-mercaptonicotinate and 0.98 g of ethyl 4-bromobutyrate provided, after alkaline hydrolysis, 1.0 g of title compound of melting point 185° C.

$^1$H—NMR (d$_6$-DMSO):

δ (ppm) = 2.0 (q, —CH$_2$CH$_2$CH$_2$—, 2H)
= 2.3 and 3.2 (each t, —CH$_2$CH$_2$CH$_2$—, 4H)
= 7.3, 8.0 and 8.7 (m, pyridine-H, 3H)

EXAMPLE 64

5-(4-Chlorobenzylthio)-1,3-thiazol-4-ylcarboxylic acid 13 g of the methyl ester of the title compound are dissolved in 300 ml of methanol. 2 g of NaOH dissolved in 10 ml of water are added to this, and the mixture is heated on a steam bath for 30 min. The Na salt of the acid crystallizes out on cooling. The solvent is removed in vacuo, the residue is taken up in water, and the solution is acidified with 2 N HCL. After filtration and drying, 11 g of product of melting point 176°–178° C. are obtained.

| Elemental analysis (C$_{11}$H$_8$NO$_2$S$_2$Cl × 0.7 H$_2$O; 298.3) | | | | |
|---|---|---|---|---|
| calculated | C 44.3% | H 3.1% | N 4.7% | H$_2$O 4.2% |
| found | 44.6% | 3.0% | 4.7% | 4.4% |

$^1$H—NMR (d$_6$-DMSO):

δ(ppm) = 4.3 (s, CH$_2$, 2H)
= 7.3 (s, aromat. H, 4H)
= 8.9 (s, thiazole-2-H, 1H)

EXAMPLE 65

5-(2-Carbomethoxyethylthio)-1,3-thiazol-4-ylcarboxylic acid 7.8 g of tert.-butyl 5-(2-carbomethoxyethylthio)-1,3-thiazol-4-ylcarboxylate are stirred in a mixture of 100 ml of trifluoroacetic acid and 100 ml of methylene ohloride at room temperature for 30 min. The solvent is removed in vacuo, and the residue is extracted by stirring with 100 ml of ether/petroleum ether (50°–70° C.) 1/1. After filtration and drying, 6.2 g of melting point 112°–116° C. are obtained, melting point 120°–121° C. after recrystallization from ethyl acetate.

| Elemental analysis (C$_8$H$_9$NO$_4$S$_2$; 247.3) | | | | |
|---|---|---|---|---|
| calculated | C 38.9% | H 3.7% | N 5.7% | S 25.9% |

-continued

| Elemental analysis ($C_8H_9NO_4S_2$; 247.3) | | | | |
|---|---|---|---|---|
| found | 38.9% | 3.8% | 5.4% | 25.8% |

$^1$H—NMR (d$_6$-DMSO):

δ(ppm) = 2.7 and 3.2 (each t, —S—CH$_2$CH$_2$—COO, 4H)
= 3.6 (s, COOCH$_3$, 3H)
= 8.8 (s, thiazole-2-H, 1H)

EXAMPLE 66

Methyl 2-(3-carboxypropylthio)-4-methyl-1,3-thiazol-5-yl-acetate

Stage 1

Methyl -2-(3-(4-methoxybenzyloxycarbonyl)propylthio)-4-methyl-1,3-thiazol-5-ylacetate 10.2 g of methyl 2-mercapto-4-methyl-1,3-thiazol-5-yl-acetate are dissolved in 200 ml of acetone, and the solution is vigorously stirred with 12.1 g of 4-methoxybenzyl 4-chlorobutyrate in the presence of 13.0 g of powdered, dry potassium carbonate (potash) while maintaining the ambient temperature. After filtration, acetone is removed in vacuo, and the residue is purified by column chromatography (SiO$_2$, ethyl acetate/cyclohexane 1:1).

Yield: 21 g of oily compound

δ (ppm) = 2.0 (m, —SCH$_2$CH$_2$CH$_2$COO—, 2H)
= 2.2 (s, 4-CH$_3$—thiazole, 3H)
= 2.3 and 3.2
(each t, —SCH$_2$CH$_2$CH$_2$COO—, 4H)
= 3.6 (s, CH$_2$COOCH$_3$, 2H)
= 3.65 and 3.7
(each s, aromat. OCH$_3$ and COOCH$_3$, each 3H)
= 4.9 (s, CH$_2$—arom., 2H)
= 6.8 and 7.2 (each d, aromat. H, 4H)

Stage 2

Title Compound 5.3 g of stage 1 are dissolved in 20 ml of trifluoroacetic acid and, after stirring for 30 min, the mixture is evaporated in vacuo. The residue is recrylstallized 2× from ethyl acetate/cyclohexane (2:1). 1.6 g of product of melting point 104°–105° C. are obtained.

| Elemental analysis ($C_{11}H_{15}NO_4S_2$; 289.3) | | | | |
|---|---|---|---|---|
| calculated | C 45.6% | H 5.2% | N 4.8% | S 22.2% |
| found | 45.3% | 5.5% | 4.7% | 22.0% |

$^1$H—NMR (CDCl$_3$)

δ (ppm) = 2.0 (m, —SCH$_2$CH$_2$CH$_2$COO—, 2H)
= 2.3 (s, 4-CH$_3$—thiazole, 3H)
= 2.4 and 3.2
(each t, —SCH$_2$CH$_2$CH$_2$COO—, 4H)
= 3.6 (s, COOCH$_3$, 3H)
= 10.8 (s, COOH, 1H, exchangeable with D$_2$O)

We claim:
1. A sulfide of the formula II

Het'—S—R$^2$    (II)

in which:
Het' represents a 1,3-thiazolyl group, or a 1,3-thiazolyl group substituted by
C$_1$–C$_6$-alkyl, or C$_1$–C$_6$-alkyl substituted by hydroxyl, C$_1$–C$_4$-alkoxy, amino, C$_1$–C$_4$-alkylamino, di-C$_1$–C$_4$-alkylamino, mercapto, C$_1$–C$_4$-alkylthio, C$_1$–C$_4$-alkoxy-carbonyl, aminocarbonyl, N-C$_1$–C$_4$-alkyl-aminocarbonyl, N,N-di-C$_1$–C$_4$-alkylaminocarbonyl, or carboxyl,
phenyl,
hydoxyl, oxo, oxido,
C$_1$–C$_4$-alkoxy,
amino,
C$_1$–C$_4$-alkylamino,
C$_1$–C$_4$-di-alkylamino,
C$_2$–C$_5$-acylamino,
C$_2$–C$_4$-alkenyl, or C$_2$–C$_4$-alkenyl substituted by C$_1$–C$_4$-alkoxy, C$_1$–C$_4$-alkoxycarbonyl, aminocarbonyl, N-C$_1$–C$_4$-alkyl-aminocarbonyl, N,N-di-C$_1$–C$_4$-alkyl-aminocarbonyl, or carboxyl,
carboxyl or
C$_1$–C$_4$-alkoxycarbonyl; and
R$^2$ represents C$_3$–C$_6$-cycloalkyl, or represents C$_1$–C$_6$-alkyl or C$_3$–C$_6$-cycloalkyl substituted by
amino, hydroxyl, carboxyl, C$_1$–C$_4$-alkoxycarbonyl, C$_1$–C$_4$-alkoxy, aminocarbonyl, oximino, oximino, C$_1$–C$_4$-alkoximino, phenyl, or phenyl substituted by
C$_1$–C$_4$-alkyl, carboxyl, aminocarbonyl, C$_1$–C$_4$-carbonyl, or halogen,
or R$^2$ represents C$_2$–C$_6$-alkenyl or C$_2$–C$_6$-alkynyl, or C$_2$–C$_6$-alkenyl or C$_2$–C$_6$-alkynyl substituted by
amino, hydroxyl, carboxyl, C$_1$–C$_4$-alkoxycarbonyl, C$_1$–C$_4$-alkoxy, aminocarbonyl, phenyl or phenyl substituted by
C$_1$–C$_4$-alkyl, carboxyl, aminocarbonyl, C$_1$–C$_4$-alkoxycarbonyl, or halogen,
with the proviso that the 1,3-thiazolyl group
(a) is not substituted by 4,5-dimethyl or 4,5-diphenyl,
(b) is not monsubstituted by methyl either in the 4- or in the 5-position, and
(c) is not unsubstituted if the substituent in the 2-position is carboxy-propylthio.
2. A compound of the formula

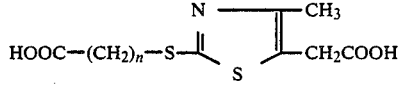

wherein n is 1–5.
3. A compound of the formula

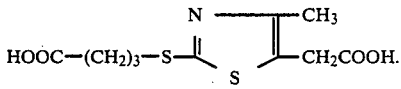

4. A pharmaceutical composition for immunostimulation or immunoenhancement containing a compound of the formula II as defined in claim 1 and a pharmaceutically acceptable carrier.
5. A pharmaceutical composition as claimed in claim 4, which additionally contains one or more substances active against infections caused by bacteria, fungi or viruses.

6. A method for the treatment of a warm-blooded mammal in need of immunostimulation or immunoenhancement which comprises administering to said mammal a pharmaceutically effective amount for said treatment of the pharmaceutical composition of claim 5.

7. A method for the treatment of a warm-blooded mammal in need of immunostimulation or immunoehancement which comprises administering to said mammal a pharmaceutically effective amount for said treatment of the pharmaceutical composition of claim 4.

8. A method for the treatment of a warm-blooded mammal in need of immunostimulation or immunoenhancement which comprises administering to said mammal a pharmaceutically effective amount for said treatment of the sulfide of the formula II as defined in claim 1.

9. A pharmaceutical composition for immunostimulation or immunoenhanement containing a compound of the formula as defined in claim 2 and a pharmaceutically acceptable carrier.

10. A pharmaceutical composition as claimed in claim 9, which additionally contains one or more substances active against infections caused by bacteria, fungi or viruses.

11. A method for the treatment of a warm-blooded mammal in need of immunostimulation or immunoenhancement which comprises administering to said mammal a pharmaceutically effective amount for said treatment of the pharmaceutical composition of claim 10.

12. A method for the treatment of a warm-blooded mammal in need of immunostimulation or immunoenhancement which comprises administering to said mammal a pharmaceutically effective amount for said treatment of the pharmaceutical composition of claim 9.

13. A method for the treatment of a warm-blooded mammal in need of immunostimulation or immunoenhancement which comprises administering to said mammal a pharamceutically effective amount for said treatment of the compound of claim 2.

14. A pharmaceutical composition for immunostimulation or immunoenhancement containing a compound of the formula as defined in claim 3 and a pharmaceutically acceptable carrier.

15. A pharmaceutical composition as claimed in claim 14, which additionally contains one or more substances active against infections caused by bacteria, fungi or viruses.

16. A method for the treatment of a warm-blooded mammal in need of immunostimulation or immunoenhancement which comprises administering to said mammal a pharmaceutically effective amount for said treatment of the pharmaceutical composition of claim 15.

17. A method for the treatment of a warm-blooded mammal in need of immunostimulation or immunoenhancement which comprises administering to said mammal a pharmaceutically effective amount for said treatment of the pharmaceutical composition of claim 14.

18. A method for the treatment of a warm-blooded mammal in need of immunostimulation or immunoenhancement which comprises administering to said mammal a pharmaceutically effective amount for said treatment of the compound of claim 3.

* * * * *